United States Patent
Peng et al.

(10) Patent No.: US 9,573,879 B2
(45) Date of Patent: Feb. 21, 2017

(54) MONOESTERS, INNER COMPLEX SALTS OR MONOESTER SALTS OF HEXAHYDRO-BETA-ACID AND APPLICATION THEREOF AS ANIMAL FEED ADDITIVES

(71) Applicant: GUANGZHOU INSIGHTER BIOTECHNOLOGY CO., LTD., Luogang, Guangzhou, Guangdong (CN)

(72) Inventors: Xianfeng Peng, Guangzhou (CN); Zonghua Qin, Guangzhou (CN); Jijun Huang, Guangzhou (CN)

(73) Assignee: GUANGZHOU INSIGHTER BIOTECHNOLOGY CO., LTD., Guangdong (CN)

( * ) Notice: Subject to any disclaimer, the term of this patent is extended or adjusted under 35 U.S.C. 154(b) by 0 days.

(21) Appl. No.: 15/119,288

(22) PCT Filed: Mar. 19, 2014

(86) PCT No.: PCT/CN2014/073654
§ 371 (c)(1),
(2) Date: Aug. 16, 2016

(87) PCT Pub. No.: WO2015/123905
PCT Pub. Date: Aug. 27, 2015

(65) Prior Publication Data
US 2016/0368853 A1 Dec. 22, 2016

(30) Foreign Application Priority Data

Feb. 19, 2014 (CN) .......................... 2014 1 0056734

(51) Int. Cl.
C07C 69/12 (2006.01)
C07F 1/08 (2006.01)
(Continued)

(52) U.S. Cl.
CPC .............. *C07C 69/12* (2013.01); *A23K 20/10* (2016.05); *A23K 20/121* (2016.05);
(Continued)

(58) Field of Classification Search
None
See application file for complete search history.

(56) References Cited

U.S. PATENT DOCUMENTS 4,190,604 A 2/1980 Burckhardt et al.
5,370,863 A * 12/1994 Barney .................. A61K 8/347
424/49

(Continued)

FOREIGN PATENT DOCUMENTS

CN 102481000 A 6/2012
EP 2 429 311 A2 3/2012
(Continued)

OTHER PUBLICATIONS

International Search Report dated Nov. 19, 2014, issued in counterpart International Application No. PCT/CN2014/073654 (2 pages).

*Primary Examiner* — Karl J Puttlitz
(74) *Attorney, Agent, or Firm* — Westerman, Hattori, Daniels & Adrian, LLP

(57) ABSTRACT

Disclosed are monoesters, inner complex salts or monoester salts of hexahydro-β-acid, and application thereof as animal feed additives. The compounds as shown in formula (I), (II) and (III) show low toxicity or non-toxicity to animals, and have higher stability and better growth promotion effects than those disclosed in other patents, which make them more suitable to be applied as growth promoters used in feed and have a very good application prospect in cultivation industry.

15 Claims, 19 Drawing Sheets

Figure 1:
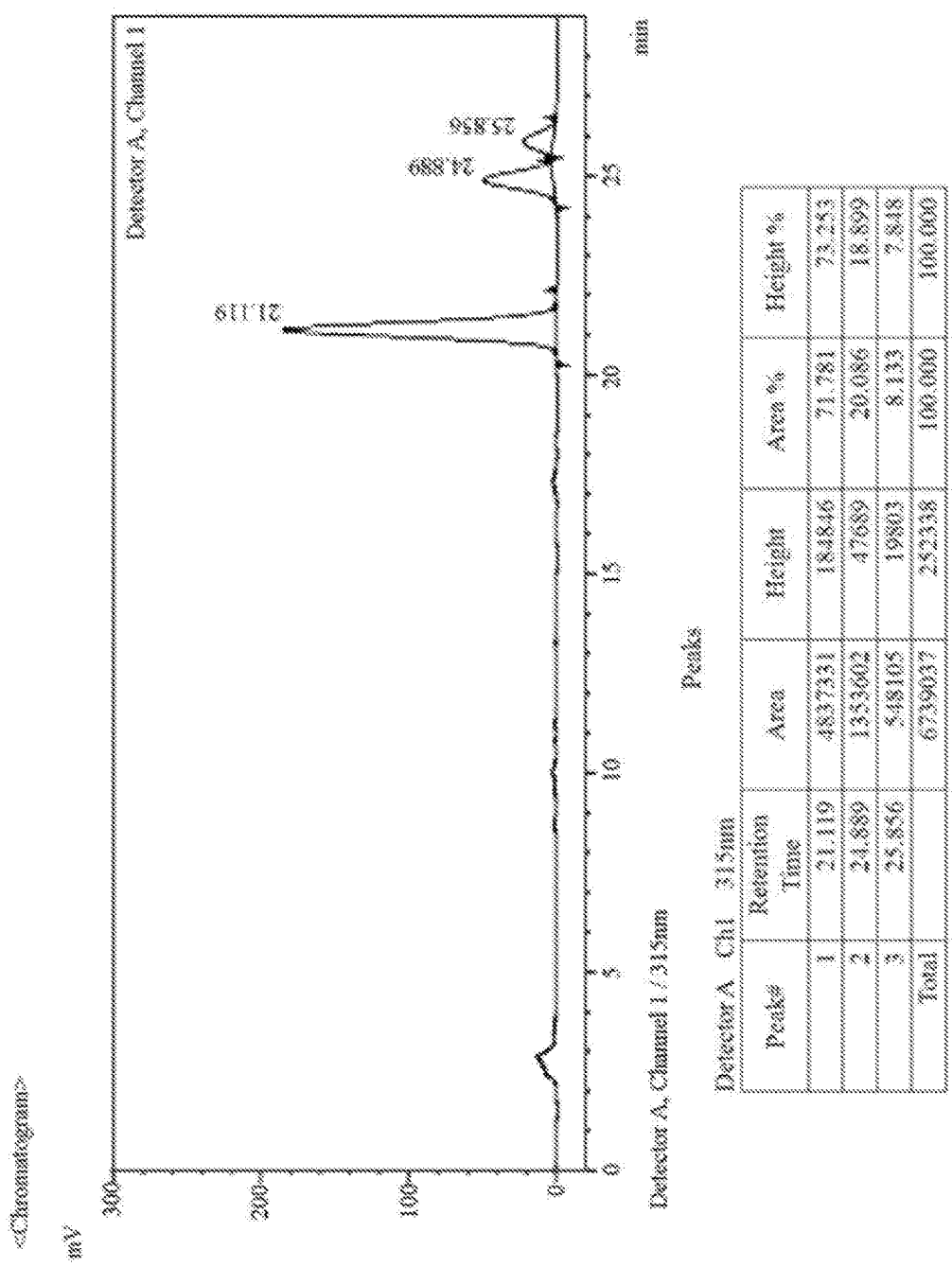

(51) Int. Cl.

| | | |
|---|---|---|
| *C07F 3/02* | (2006.01) | |
| *C07F 3/00* | (2006.01) | |
| *C07F 3/06* | (2006.01) | |
| *C07F 13/00* | (2006.01) | |
| *C07F 15/06* | (2006.01) | |
| *C07F 15/02* | (2006.01) | |
| *C07C 49/713* | (2006.01) | |

(52) U.S. Cl.
CPC .............. *C07C 49/713* (2013.01); *C07F 1/08* (2013.01); *C07F 3/003* (2013.01); *C07F 3/02* (2013.01); *C07F 3/06* (2013.01); *C07F 13/005* (2013.01); *C07F 15/025* (2013.01); *C07F 15/065* (2013.01); *C07C 2101/16* (2013.01)

(56) References Cited

U.S. PATENT DOCUMENTS

| | | |
|---|---|---|
| 6,251,461 B1 | 6/2001 | Johnson et al. |
| 7,090,873 B2 | 8/2006 | Maye |
| 7,553,504 B2 | 6/2009 | Rigby et al. |
| 8,012,516 B2 | 9/2011 | Rigby et al. |
| 8,197,863 B2 | 6/2012 | Maye |
| 2004/0219240 A1 | 11/2004 | Babish et al. |
| 2006/0083775 A1 | 4/2006 | Rigby et al. |
| 2006/0134248 A1 | 6/2006 | Maye |
| 2006/0269588 A1 | 11/2006 | Maye |
| 2008/0213342 A1 | 9/2008 | Maye |
| 2011/0311663 A1 | 12/2011 | Rigby et al. |
| 2012/0115960 A1 | 5/2012 | Garden et al. |
| 2013/0018106 A1 | 1/2013 | Maye |

FOREIGN PATENT DOCUMENTS

| | | |
|---|---|---|
| EP | 2 606 742 A1 | 6/2013 |
| EP | 1 542 543 B1 | 11/2013 |
| EP | 1 722 635 B1 | 11/2015 |
| WO | 2010/123571 | * 10/2010 |
| WO | 2010/123571 A2 | 10/2010 |

* cited by examiner

MONOESTERS, INNER COMPLEX SALTS OR MONOESTER SALTS OF HEXAHYDRO-BETA-ACID AND APPLICATION THEREOF AS ANIMAL FEED ADDITIVES

FIELD OF THE INVENTION

The present invention relates to the field of feed for poultry and livestock, specifically to monoesters, inner complex salts or monoester salts of hexahydro-β-acid and application thereof as animal feed additives.

BACKGROUND OF THE INVENTION

A plurality of US patents, such as U.S. Pat. No. 8,197,863B2, U.S. Pat. No. 8,012,516B2, US20080213342A1, US20060269588, US20040219240, U.S. Pat. No. 7,090,873, US20060134248, US20110311663, U.S. Pat. No. 7,553,504, US20130018106 and U.S. Pat. No. 6,251,461, and as plurality of European patents, such as EP2606742A1, EP1542543B1, EP2429311A2 and EP1722635B1, have disclosed the application of hops acids and hydrogenated β-acids as substitutes for antibiotic growth promoters used in feed.

However, recited in the above-mentioned patents is the application of extracts from hops or hops acids (e.g. a mixture of α-acids and β-acids) as feed additives those already included in the Chinese Feed Additive Catalogue but only serve as condiment for feed. Secondly, the grounds of the patents are mainly results of trial in vitro rather than feeding trial. What's more, there is no data so far, to demonstrate safety and stability of these natural products, or the salts and ester thereof, as animal feed additives.

Hexahydro-β-acids are also mentioned in the above-mentioned patents, but application of the esters, salts or ester salts thereof as animal feed additives has not been reported so far.

SUMMARY OF THE INVENTION

The first object of the present invention is to provide inner complex salts, monoesters, or acetate ester salts of hexahydro-β-acids which are more stable, can promote the growth of animals, and are preferable to be used as feed additives.

The inner complex salts of hexahydro-β-acid of the present invention have a structural formula as shown in formula (I).

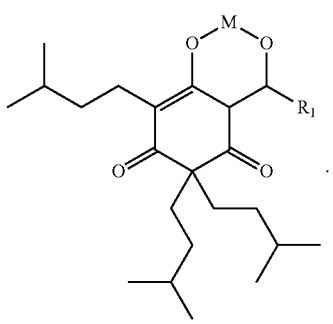

Formula (I)

$R_1$ is isopropyl, isobutyl or sec-butyl; M is a divalent metal ion of, e.g. copper, zinc, manganese, cobalt, iron, calcium or magnesium.

The acetate ester salts of hexahydro-β-acid of the present invention have a structural formula as shown in formula (II).

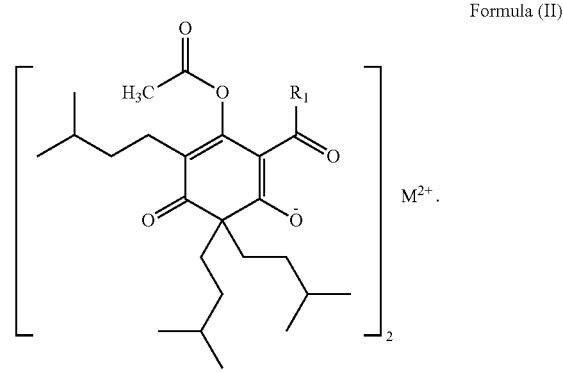

Formula (II)

$R_1$ is isopropyl, isobutyl or sec-butyl; M is a divalent metal ion of e.g. copper, zinc, manganese, cobalt, iron, calcium or magnesium.

The acetate ester salts of hexahydro-β-acid mainly refer to the salts formed by the coordination between a divalent metal (such as copper, zinc, manganese, cobalt, calcium or magnesium) ion and two phenolic hydroxyl groups separately in two acetate esters of hexahydro-β-acid.

The monoesters of hexahydro-β-acids of the present invention have a structural formula as shown in formula (III).

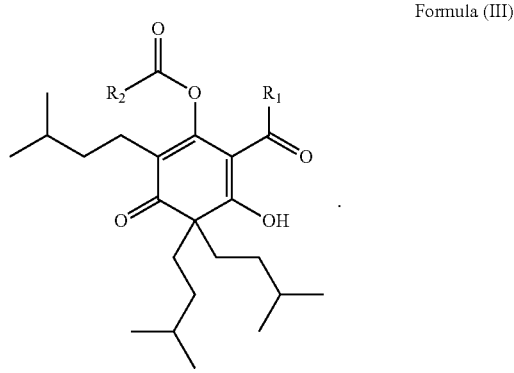

Formula (III)

$R_1$ is isopropyl, isobutyl or sec-butyl; $R_2$ is $—(CH_2)_nCH_3$, and n=0~16.

The present invention also includes an application of the above-mentioned inner complex salts, acetate ester salts or monoesters of hexahydro-β-acid in preparation of animal growth-promoting feed additives.

Said animal includes pig, chickens, ducks, geese, beef cattle, dairy cattle, sheep, fish, shrimp, foxes, martens or raccoon dogs, in all growth stages.

The animal growth-promoting feed is complete formula feed. A dosage of the compound as shown in formula (I), (II) or (III) as animal growth-promoting feed additive is 0.1~200 ppm in the complete formula feed.

The hexahydro-β-acid mainly includes hexahydrolupulone, hexahydroadlupulone and hexahydrocolupulone, which are disclosed in prior art.

The inner complex salts of hexahydro-β-acid refer to the inner complex salts formed by the coordination between a divalent metal (such as copper, iron, zinc, manganese, cobalt, calcium or magnesium) ion and two phenolic hydroxyl groups in the same hexahydro-β-acid. The acetate ester salts of hexahydro-β-acid include calcium salt, magnesium salt, copper salt, zinc salt, manganese salt, iron salt and cobalt salt of acetate ester of hexahydro-β-acid.

The monoesters of hexahydro-β-acid include the esters ranged from acetate ester to hexadecanoate ester of hexahydro-β-acid.

The compounds of the present invention as shown in formula (I), (II) and (III) show low toxicity or non-toxicity to animals, and have higher stability and better growth promotion effects than those disclosed in other patents, which make them more suitable to be applied as growth promoters used in feed and have a very good application prospect in cultivation industry.

DETAILED DESCRIPTION OF THE EMBODIMENTS

The present invention is described in further detail with reference to embodiments which shall not be regarded as limits to the present invention.

Embodiment 1

Extraction of β-acid 1 kg of hop extracts, 1 L of absolute ethanol, and 90 g of potassium hydroxide (which was dissolved in 100 ml of water) were added into a 5 L vessel, and stirred at room temperature to give a uniform mixture. The mixture was added with 3 L of tap water with stirring, stirred for one hour, let stand for 30 minutes, and filtrated to remove grease and insolubles. The filtrate was collected, and the layers were separated. $CO_2$ gas was passed through the water phase to give a great amount of precipitate. Then the water phase was added with 1.2 L of aqueous solution of 10% potassium hydroxide, followed by addition of 200 mL of n-hexane, and the layers were separated. The organic phase and the oil layer were removed. The water phase was collected, adjusted with aqueous solution of 20% phosphate acid, and extracted with 1 L of n-hexane. The resulting organic phase was concentrated in vacuum to give about 400 g of crude product of β-acid (the content was about 90%).

Embodiment 2: Synthesis of hexahydro-β-acid

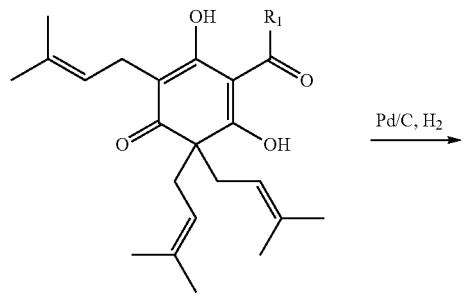

Pd/C, H$_2$

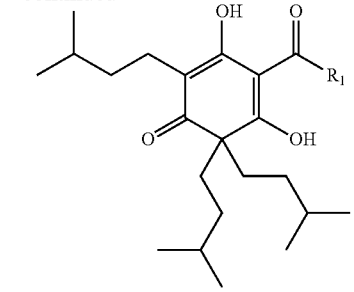

$R_1$ = —CH(CH$_3$)$_2$, —CH$_2$CH(CH$_3$)$_2$, —CH(CH$_3$)(CH$_2$CH$_3$)

To a hydrogenation reactor was added about 360 g of the crude product of β-acid, followed by 95% ethanol to afford a total volume of 2.5 L, and eventually 36 g of 10% palladium on carbon. Agitation began and the reactor were purged with nitrogen for three times and then with hydrogen for three times. Then the reaction was continued for 12~15 hours at room temperature under a pressure of 0.6~0.7 MPa. After the reaction was complete, the resulting solution was filtrated to remove the palladium on carbon. The filtrate was concentrated in vacuum to remove ¾ of the solvent, added with 3.5 L tap water with stirring, stirred for about 1~2 hours, and then subjected to suction filtration. The solids were collected as hexahydro-β-acid, about 340 g after being dried over night at 50° C.

Embodiment 3

Synthesis of Inner Complex Salts of Hexahydro-β-acid

Synthesis of salt derivatives of the hexahydro-β-acid is as shown below, wherein the first step is the formation of potassium salt by the reaction between hydroxyl group and potassium hydroxide, followed by the formation of corresponding salt by replacing the potassium with other metal.

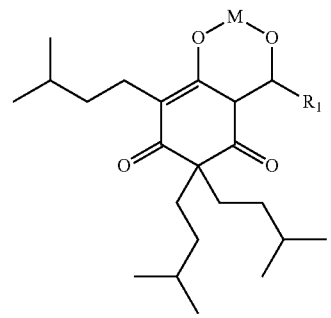

$R_1$ = —CH(CH$_3$)$_2$, —CH$_2$CH(CH$_3$)$_2$, —CH(CH$_3$)(CH$_2$CH$_3$)

Process

Embodiment 3.1

Preparation of Copper Salt of Hexahydro-β-acid (IST_011_011)

5.0 g of hexahydro-β-acid was dissolved in 15 ml of 95% ethanol. 2.1 g of potassium hydroxide was dissolved in 32 ml of water. The potassium hydroxide solution was added dropwise into the hexahydro-β-acid solution, and the resulting mixture was stirred to give potassium salt. Then 5.0 g of copper chloride dihydrate was dissolved in 30 ml of water, and the resulting solution was added dropwise into the potassium salt solution. Then the resulting mixture was stirred for 1 hour and filtrated. The filter cake was washed with water, and dried to give 5.4 g of dark blue solids (copper salt of hexahydro-β-acid), the yield of which is about 93%.

Embodiment 3.2

Preparation of Magnesium Salt of Hexahydro-β-acid (IST_011_012)

5.0 g of hexahydro-β-acid was dissolved in 15 ml of ethanol. 1.8 g of potassium hydroxide was dissolved in 20 ml of water. The potassium hydroxide solution was added into the hexahydro-β-acid solution, and the resulting mixture was stirred for 1 hour. 2.9 g of magnesium chloride hexahydrate (1 eq) was dissolved in 20 ml of water, and the resulting solution was added dropwise into the potassium salt solution. Then the resulting mixture was stirred for 1 hour to give white solids and then filtrated. The filter cake was washed with water, and dried to give 5.0 g of white solids (magnesium salt of hexahydro-β-acid), the yield of which is about 97% (FIG. 1).

Embodiment 3.3

Preparation of Calcium Salt of Hexahydro-β-acid (IST_011_013)

Figure 2:
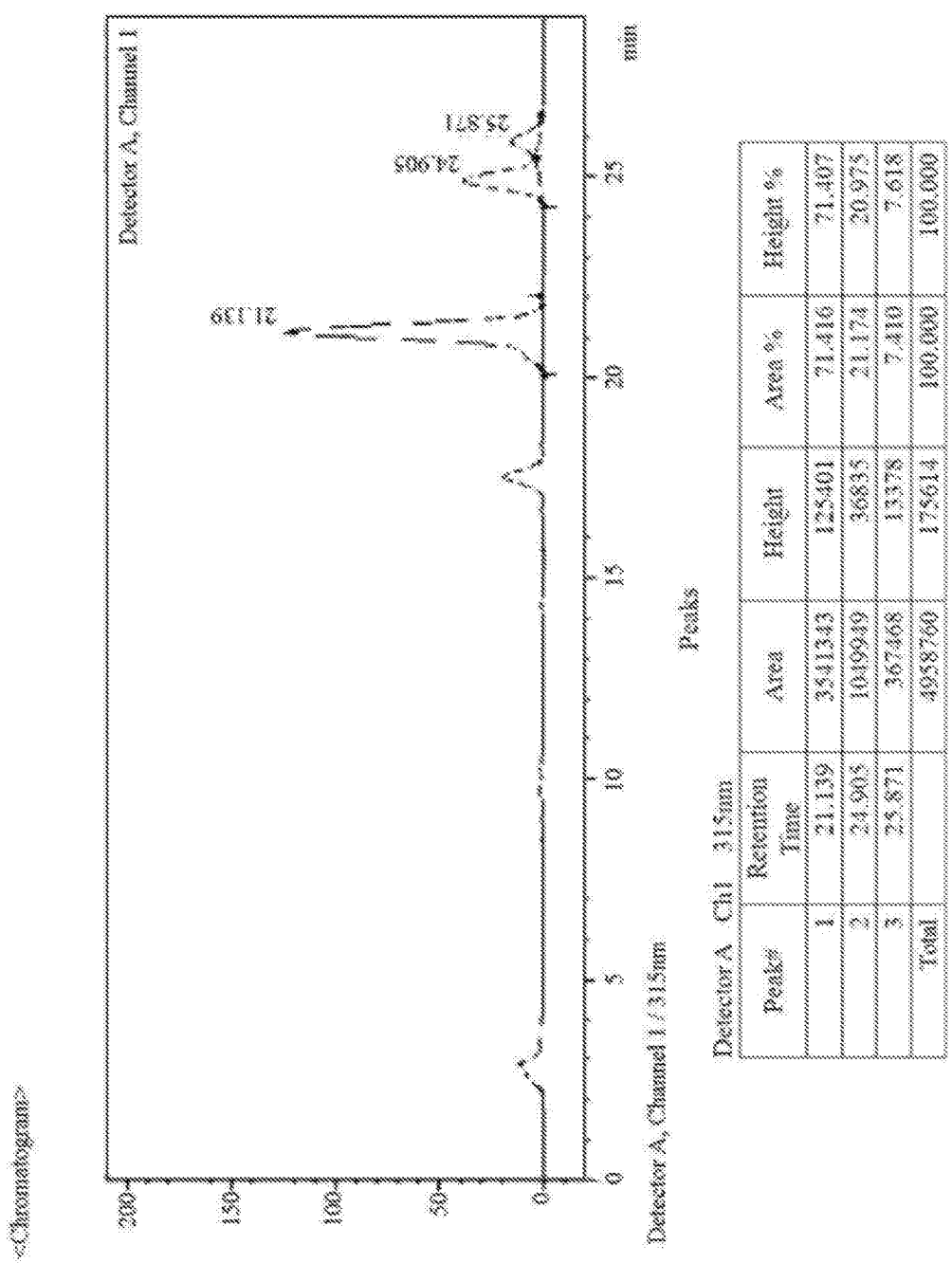

5.0 g of hexahydro-β-acid was dissolved in 15 ml of 95% ethanol. 1.9 g of potassium hydroxide was dissolved in 32 ml of water. The potassium hydroxide solution was added dropwise into the hexahydro-β-acid solution, and the resulting mixture was stirred to give potassium salt. 3.4 g of calcium chloride was dissolved in 20 ml of water, and the resulting solution was added dropwise into the potassium salt solution. Then the resulting mixture was stirred for 1 hour and filtrated. The filter cake was washed with water and dried to give 4.4 g of yellowish solids (calcium salt of hexahydro-β-acid), the yield of which is about 80% (FIG. 2).

Embodiment 3.4

Preparation of Zinc Salt of Hexahydro-β-acid (IST_011_014)

Figure 3:
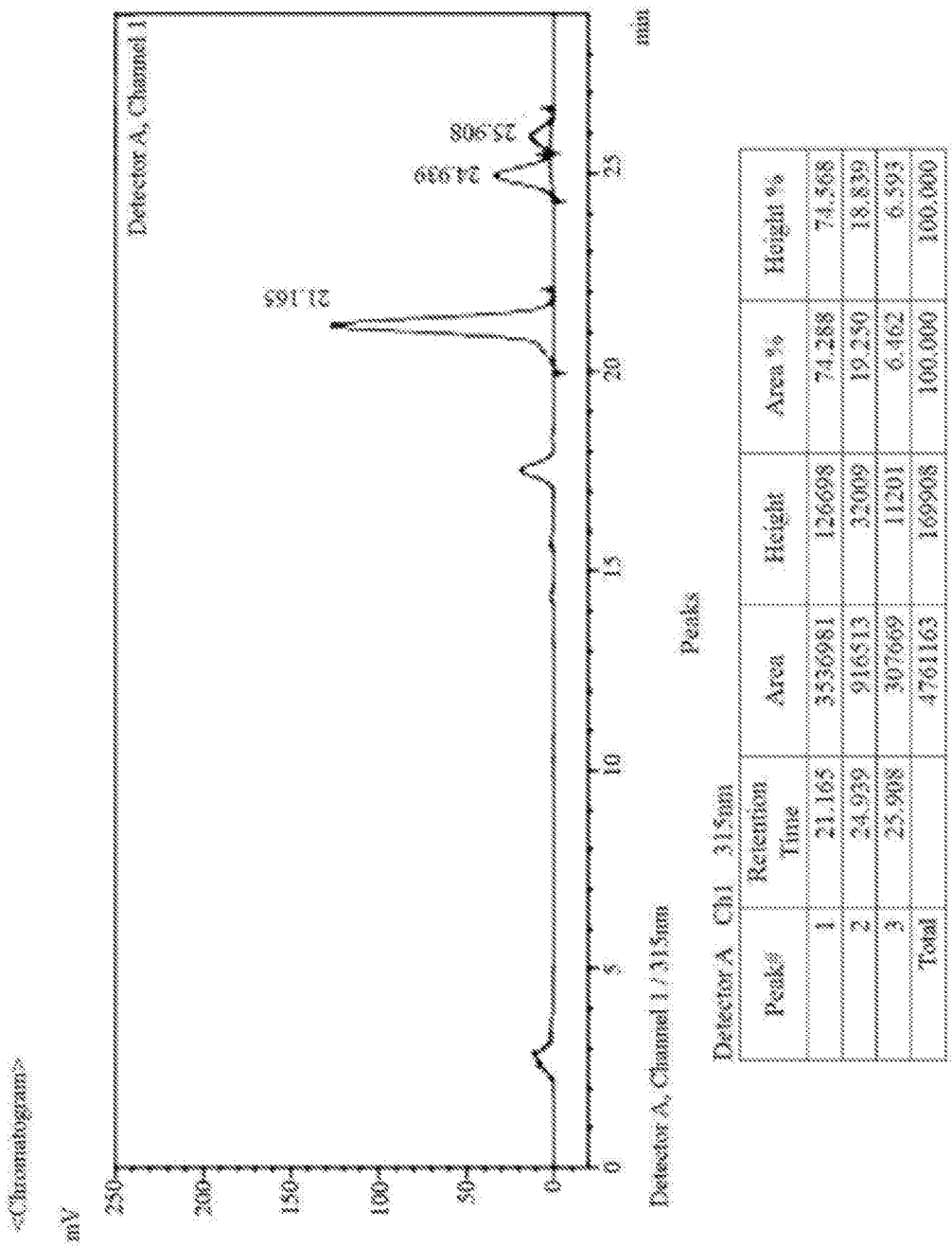

6.0 g of hexahydro-β-acid was dissolved in 15 ml of 95% ethanol, followed by addition of 1.8 g of potassium hydroxide, and then stirred to give salt. The resulting solution was added with 3.0 g of zinc chloride and stirred for 1 hour, then added dropwise with 20 ml of water and stirred for 1 hour, and added with 60 ml of water and stirred for 2 hours. Then the solution was filtrated, the filter cake was washed with water, and dried to give 6.8 g of yellowish solids (zinc salt of hexahydro-β-acid), the yield of which is about 99% (FIG. 3).

Embodiment 3.5

Preparation of Manganese Salt of Hexahydro-β-acid (IST_011_015)

Figure 4:
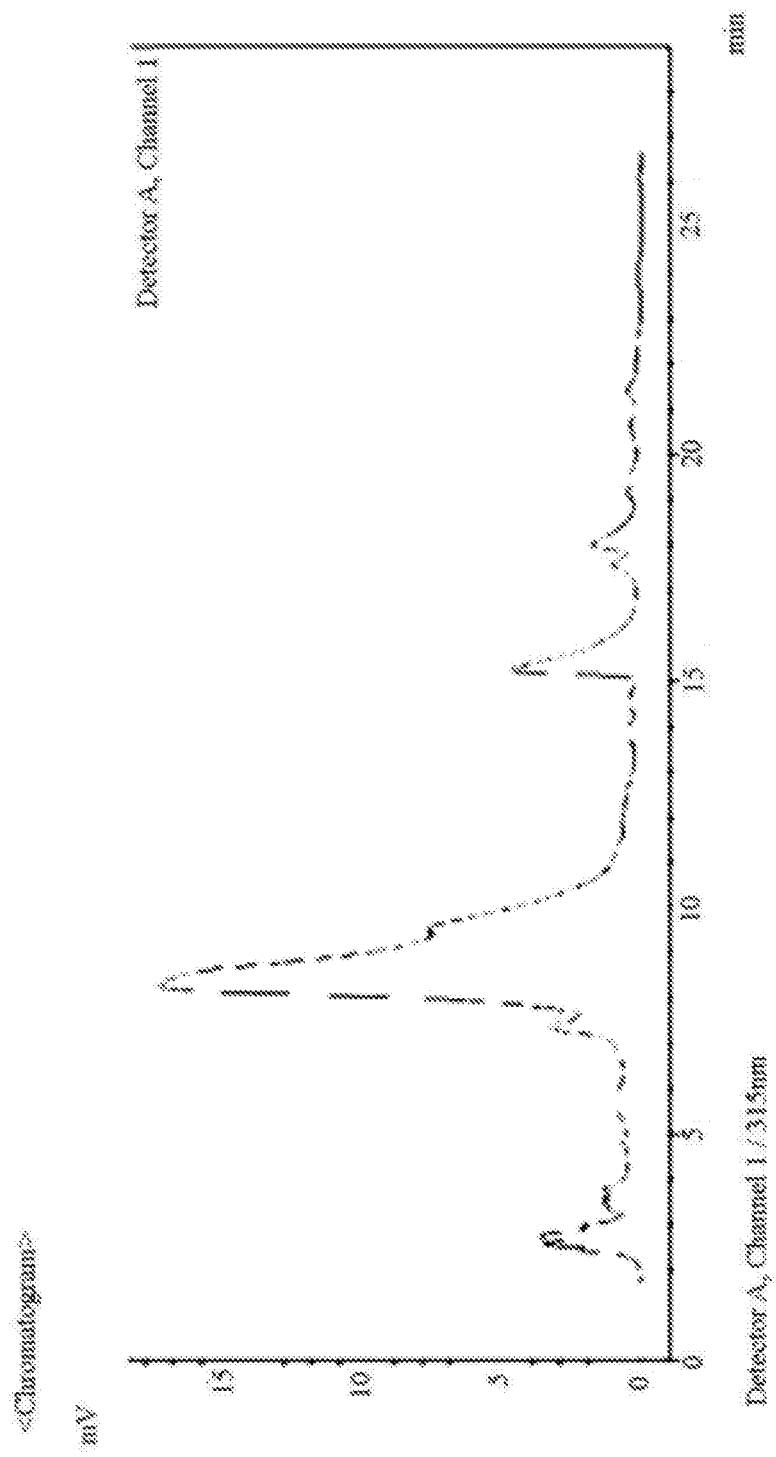

5.0 g of hexahydro-β-acid was dissolved in 15 ml of 95% ethanol. 2.0 g of potassium hydroxide was dissolved in 32 ml of water. The potassium hydroxide solution was added dropwise into the hexahydro-β-acid solution, and the resulting mixture was stirred to give potassium salt. 4.3 g of manganese chloride was dissolved in 50 ml of water, and the resulting solution was added dropwise into the potassium salt solution. Then the resulting mixture was stirred for 1 hour and filtrated. The filter cake was washed with water, and dried to give 5.6 g of yellow solids (manganese salt of hexahydro-β-acid), the yield of which is about 98% (FIG. 4).

Embodiment 3.6

Preparation of Cobalt Salt of Hexahydro-β-acid (IST_011_016)

Figure 5:
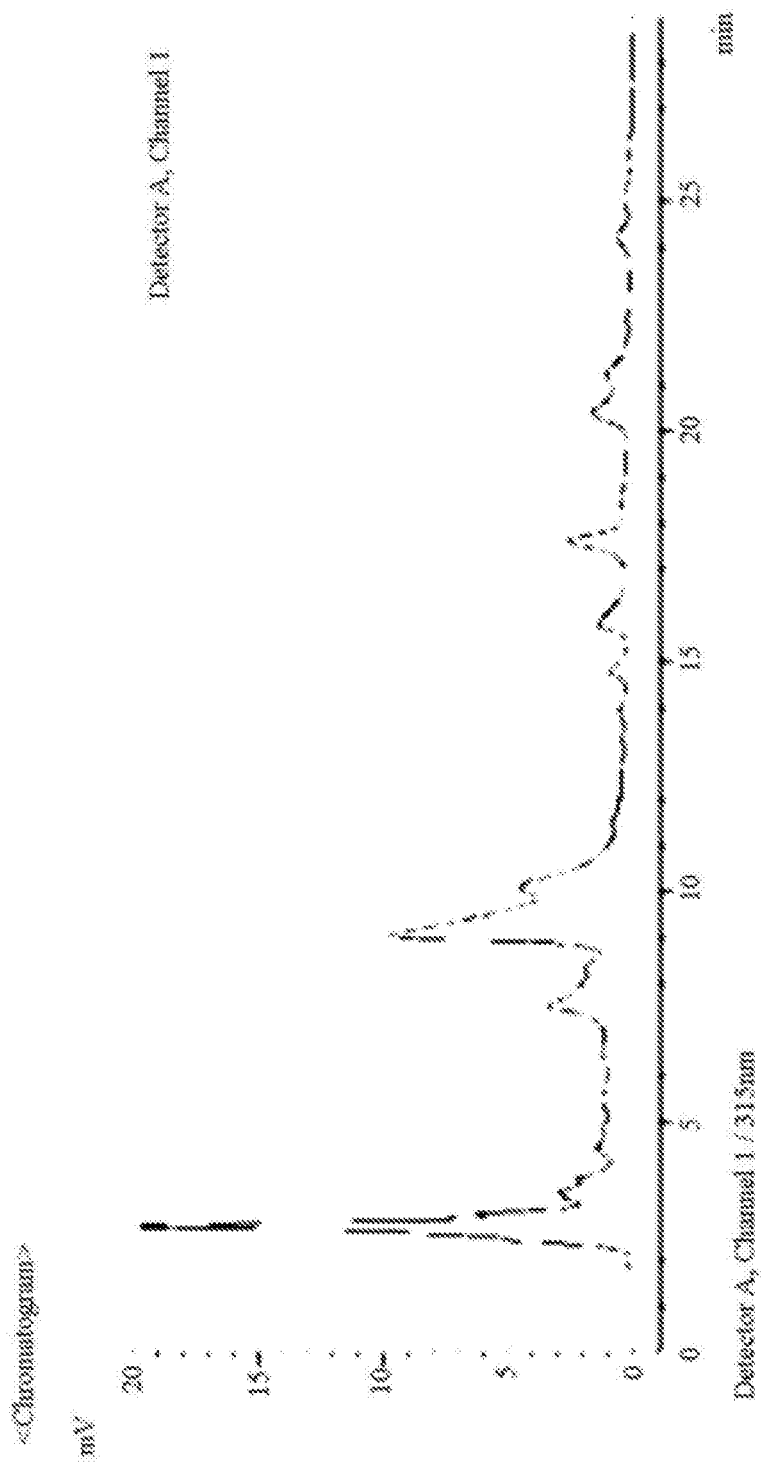

5.0 g of hexahydro-β-acid was dissolved in 15 ml of 95% ethanol. 2.0 g of potassium hydroxide was dissolved in 32 ml of water. The potassium hydroxide solution was added dropwise into the hexahydro-β-acid solution, and the resulting mixture was stirred to give potassium salt. 7.0 g of cobalt chloride hexahydrate was dissolved in 50 ml of water, and the resulting solution was added dropwise into the potassium salt solution. Then the resulting mixture was stirred for 1 hour and filtrated. The filter cake was washed with water, and dried to give 5.3 g of yellowish solids (cobalt salt of hexahydro-β-acid), the yield of which is about 93% (FIG. 5).

Embodiment 3.7

Preparation of Ferrous Salt of Hexahydro-β-acid (IST_011_017)

Figure 6:
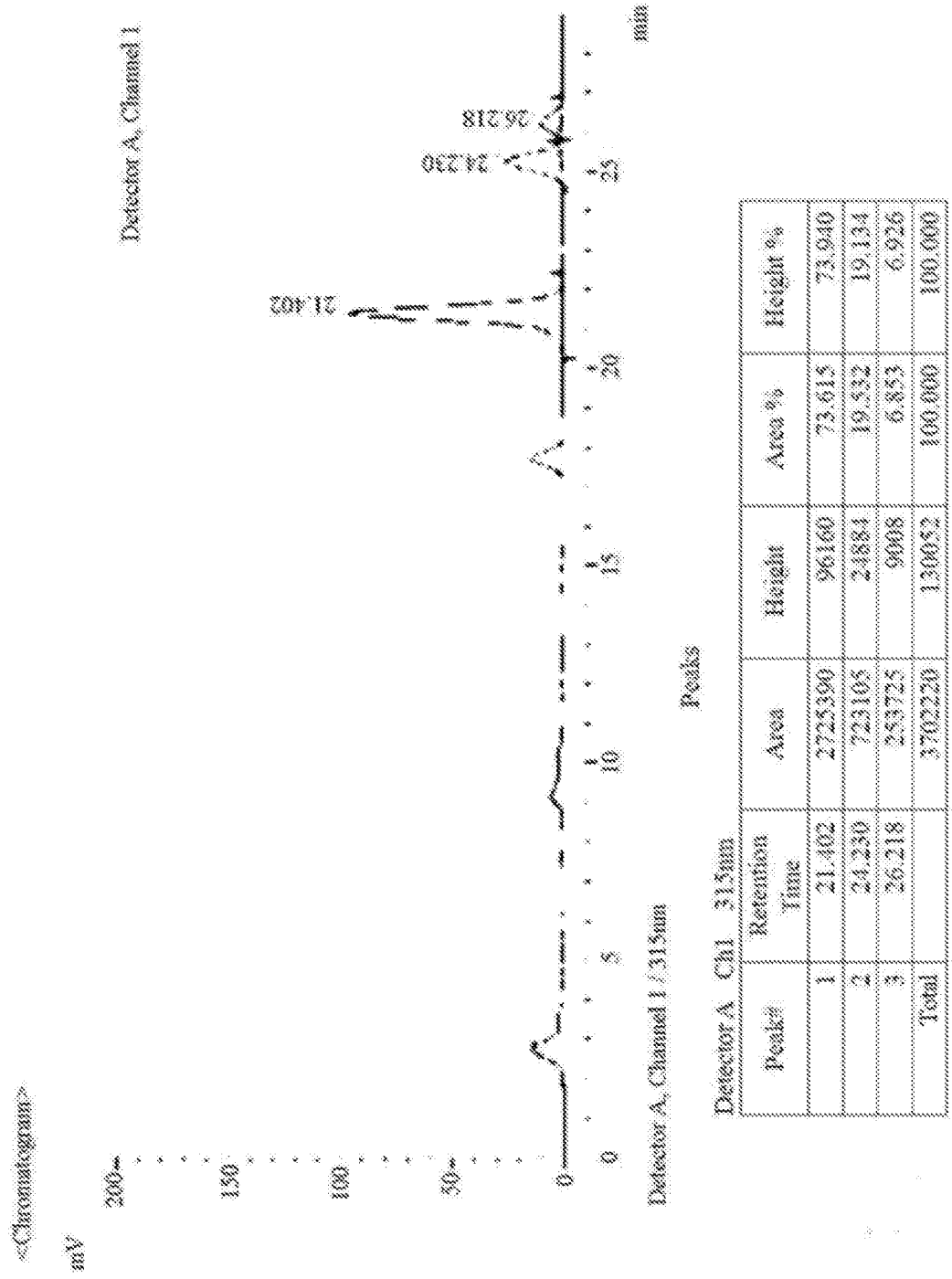

6.1 g of hexahydro-β-acid was dissolved in 24 ml of 95% ethanol, followed by addition of 2.0 g of potassium hydroxide, and then stirred to give salt. The resulting solution was added with 4.6 g of ferrous sulfate heptahydrate and stirred for 1 hour, then added dropwise with 20 ml of water and stirred for 1 hour, and added with 60 ml of water and stirred for 2 hours. Then the solution was filtrated, the filter cake was washed with water, and dried to give 6.1 g of brown solids (ferrous salt of hexahydro-β-acid), the yield of which is about 88% (FIG. 6).

Embodiment 4

Synthesis of Acetate Ester Salt Derivatives of Hexahydro-β-acid

Synthesis of acetate ester salt derivatives of hexahydro-β-acid is as shown below, wherein the first step is the formation of potassium salts by the reaction between hydroxyl group and potassium hydroxide, followed by the formation of corresponding salt by replacing the potassium with other metal.

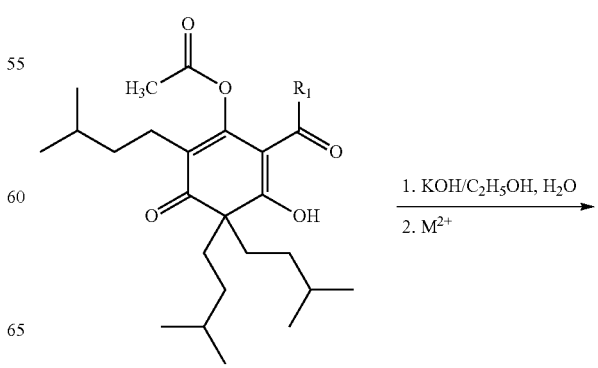

-continued

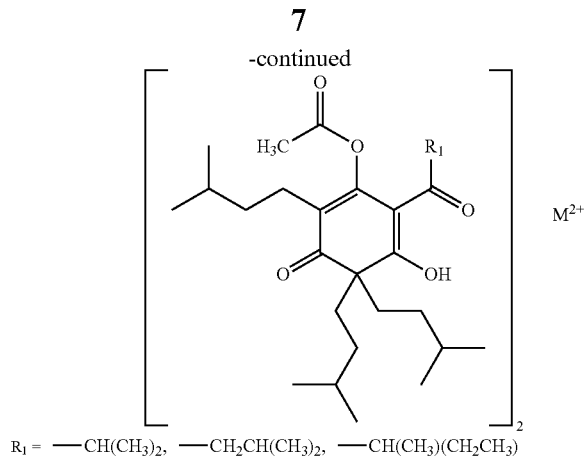

$R_1 = $ —$CH(CH_3)_2$, —$CH_2CH(CH_3)_2$, —$CH(CH_3)(CH_2CH_3)$

Process

Embodiment 4.1

Preparation of Copper Salt of Acetate Ester of Hexahydro-β-acid (IST_011_004)

Figure 7:
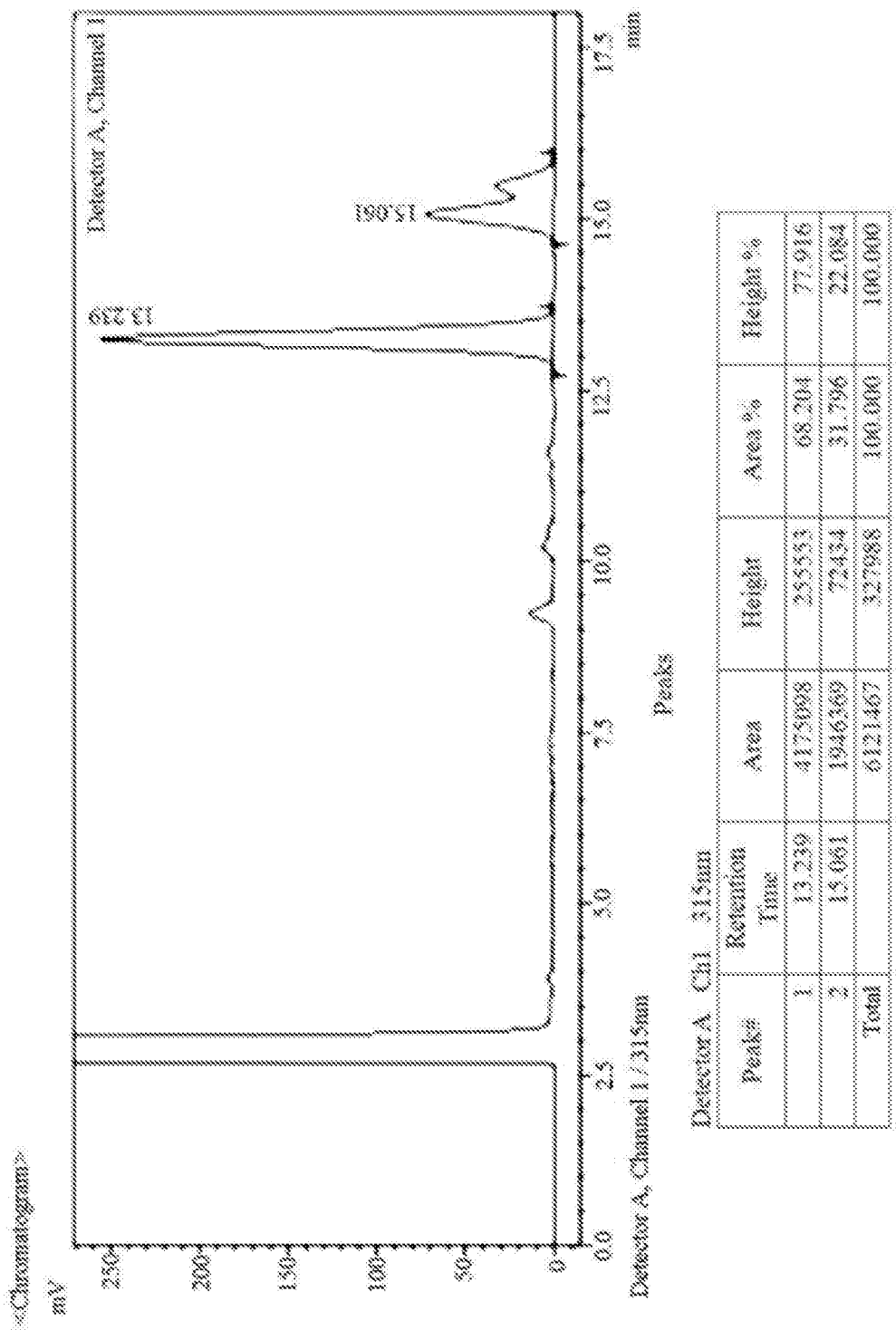

5 g of acetate ester of hexahydro-β-acid was dissolved in 40 ml of 95% ethanol. The resulting solution was cooled to 0° C. with stirring, and then added with 95 ml of aqueous solution of 1% potassium hydroxide dropwise within about 20 minutes. 2.0 g of copper chloride dihydrate was dissolved in 20 ml of water, and the resulting solution was added dropwise into the potassium solution. Then the resulting mixture was stifled for 1 hour and filtrated. The filter cake was washed with water, and dried to give 4.5 g of dark green solids (copper salt of acetate ester of hexahydro-β-acid), the yield of which is about 83% (FIG. 7).

Embodiment 4.2

Preparation of Magnesium Salt of Acetate Ester of Hexahydro-β-acid (IST_011_005)

Figure 8:
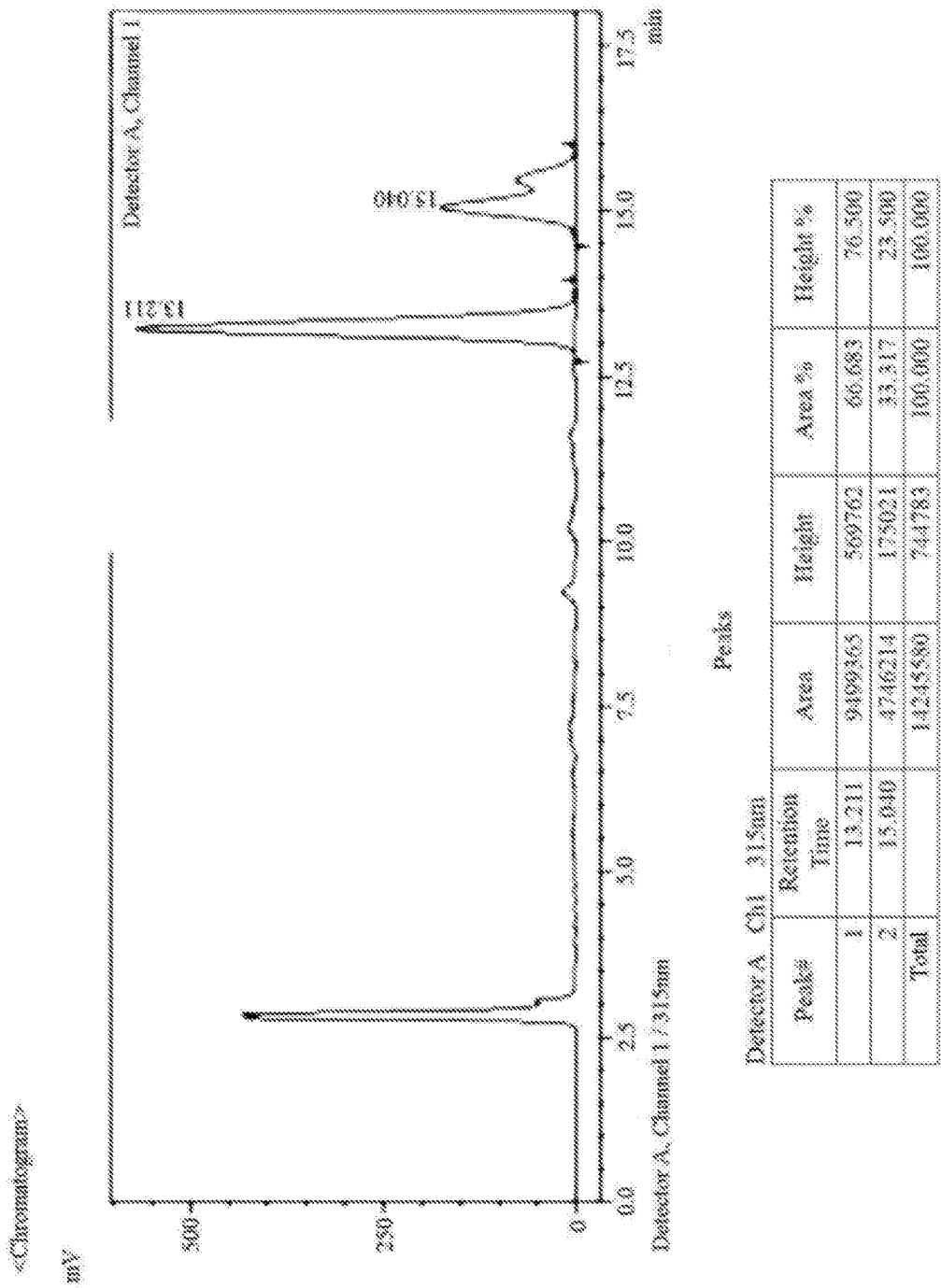

5.3 g of acetate ester of hexahydro-β-acid was dissolved in 40 ml of 95% ethanol. The resulting solution was cooled to 0° C. with stirring, and then added with 100 ml of aqueous solution of 1% potassium hydroxide dropwise within about 0.5 h. 0.98 g of magnesium sulfate was dissolved in 10 ml of water, and the resulting solution was added dropwise into the potassium solution. Then the resulting mixture was stirred for 1 hour and filtrated. The filter cake was washed with water, and dried to give 4.8 g of yellowish solids (magnesium salt of acetate ester of hexahydro-β-acid), the yield of which is about 87% (FIG. 8).

Embodiment 4.3

Preparation of Calcium Salt of Acetate Ester of Hexahydro-β-acid (IST_011_006)

Figure 9:
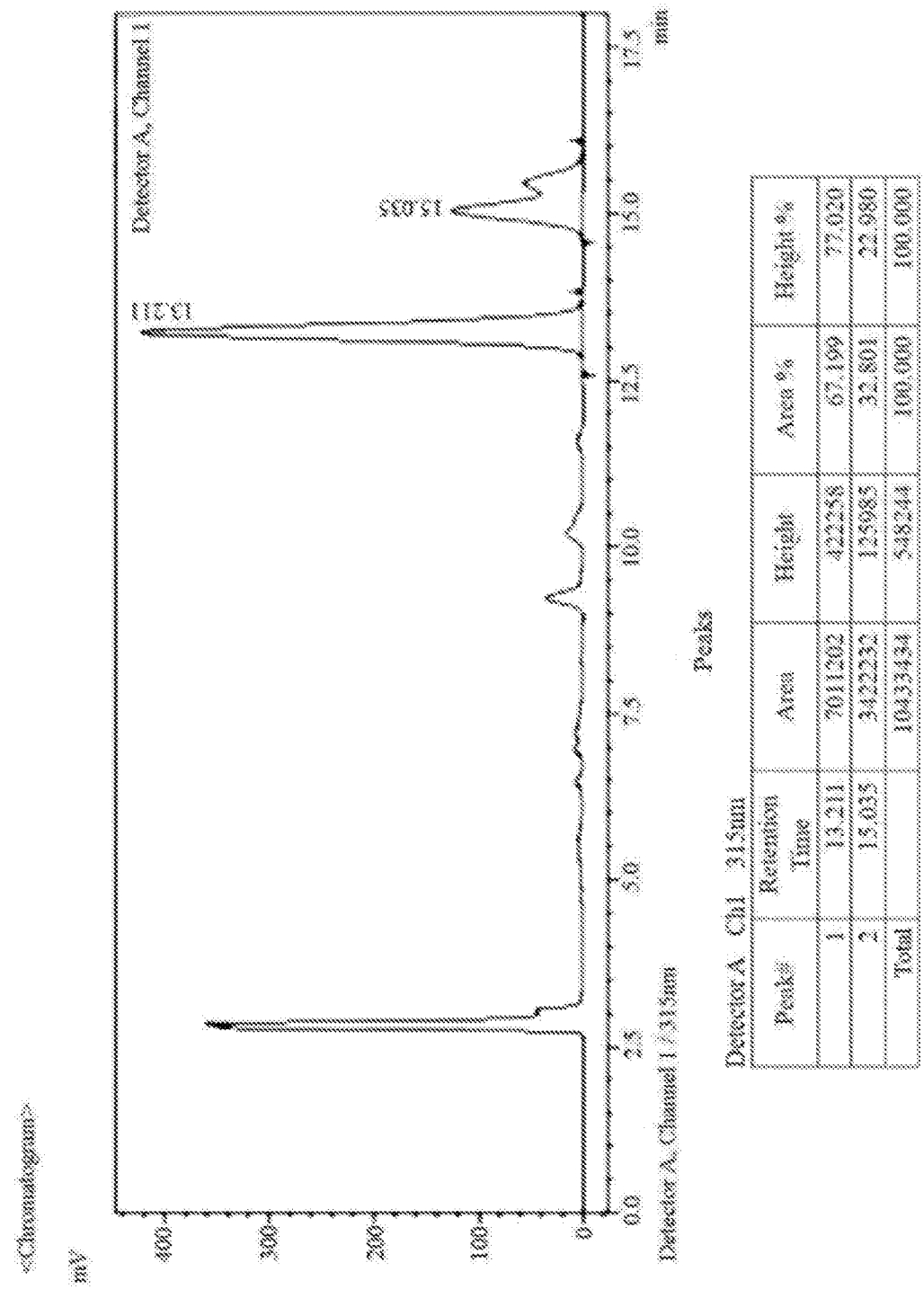

5.3 g of acetate ester of hexahydro-β-acid was dissolved in 40 ml of 95% ethanol. The resulting solution was cooled to 0° C. with stirring, and then added with 100 ml of aqueous solution of 1% potassium hydroxide dropwise within about 0.5 h. 1.0 g of calcium chloride was dissolved in 10 ml of water, and the resulting solution was added into the potassium solution. Then the resulting mixture was stirred for 1 hour and filtrated. The filter cake was washed with water, and dried to give 2.5 g of yellowish solids (calcium salt of acetate ester of hexahydro-β-acid), the yield of which is about 46% (FIG. 9).

Embodiment 4.4

Preparation of Zinc Salt of Acetate Ester of Hexahydro-β-acid (IST_011_007)

Figure 10:
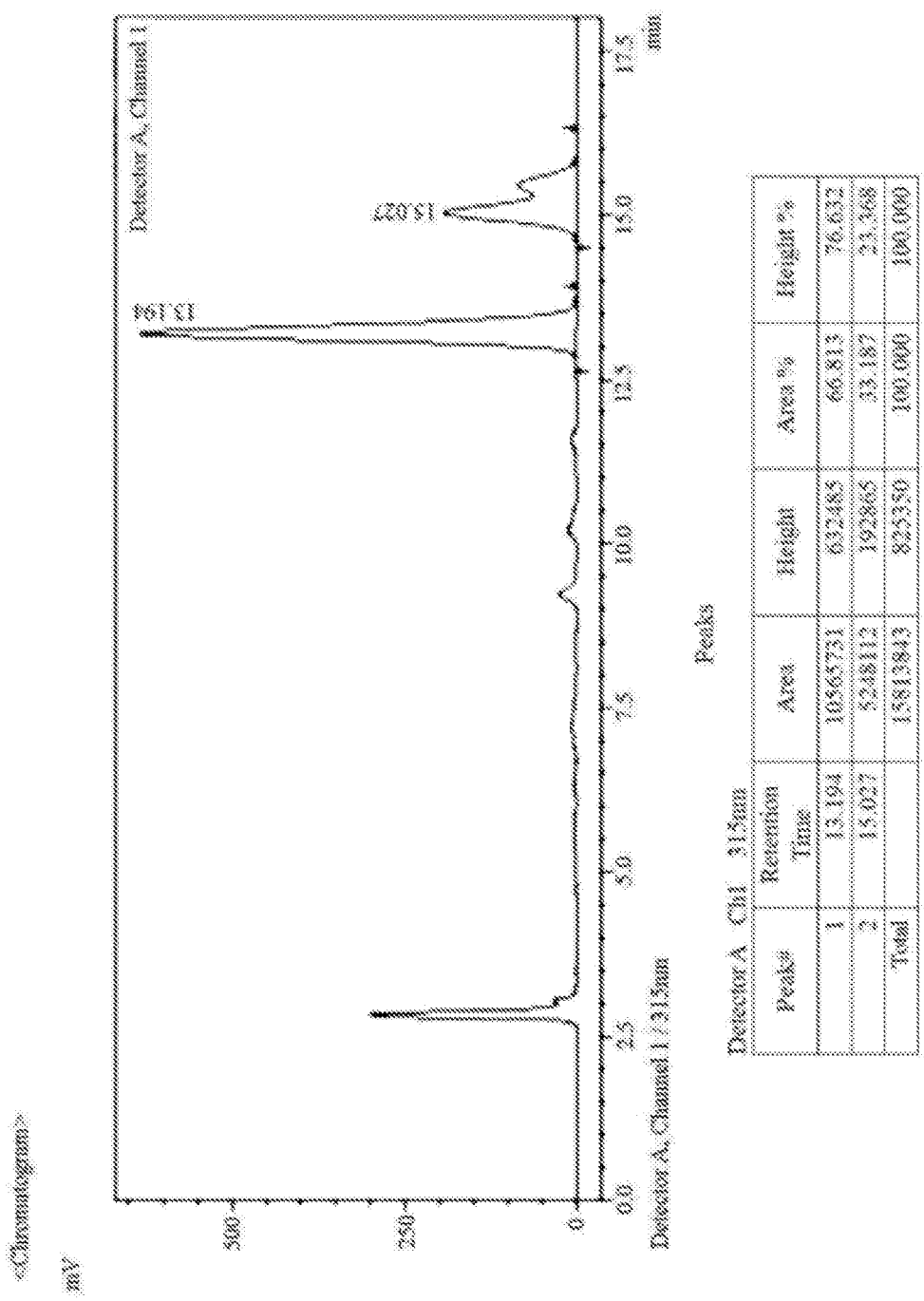

0.5 g of acetate ester of hexahydro-β-acid was dissolved in 40 ml of 95% ethanol. The resulting solution was added with 95 ml of aqueous solution of 1% potassium hydroxide dropwise within about 20 minutes. 0.9 g of zinc chloride was dissolved in 20 ml of water, and the resulting solution was added into the potassium solution. Then the resulting mixture was stirred for 1 hour and filtrated. The filter cake was washed with water, and dried to give 2.5 g of yellowish solids (zinc salt of acetate ester of hexahydro-β-acid), the yield of which is about 46% (FIG. 10).

Embodiment 4.5

Preparation of Cobalt Salt of Acetate Ester of Hexahydro-β-acid (IST_011_009)

Figure 11:
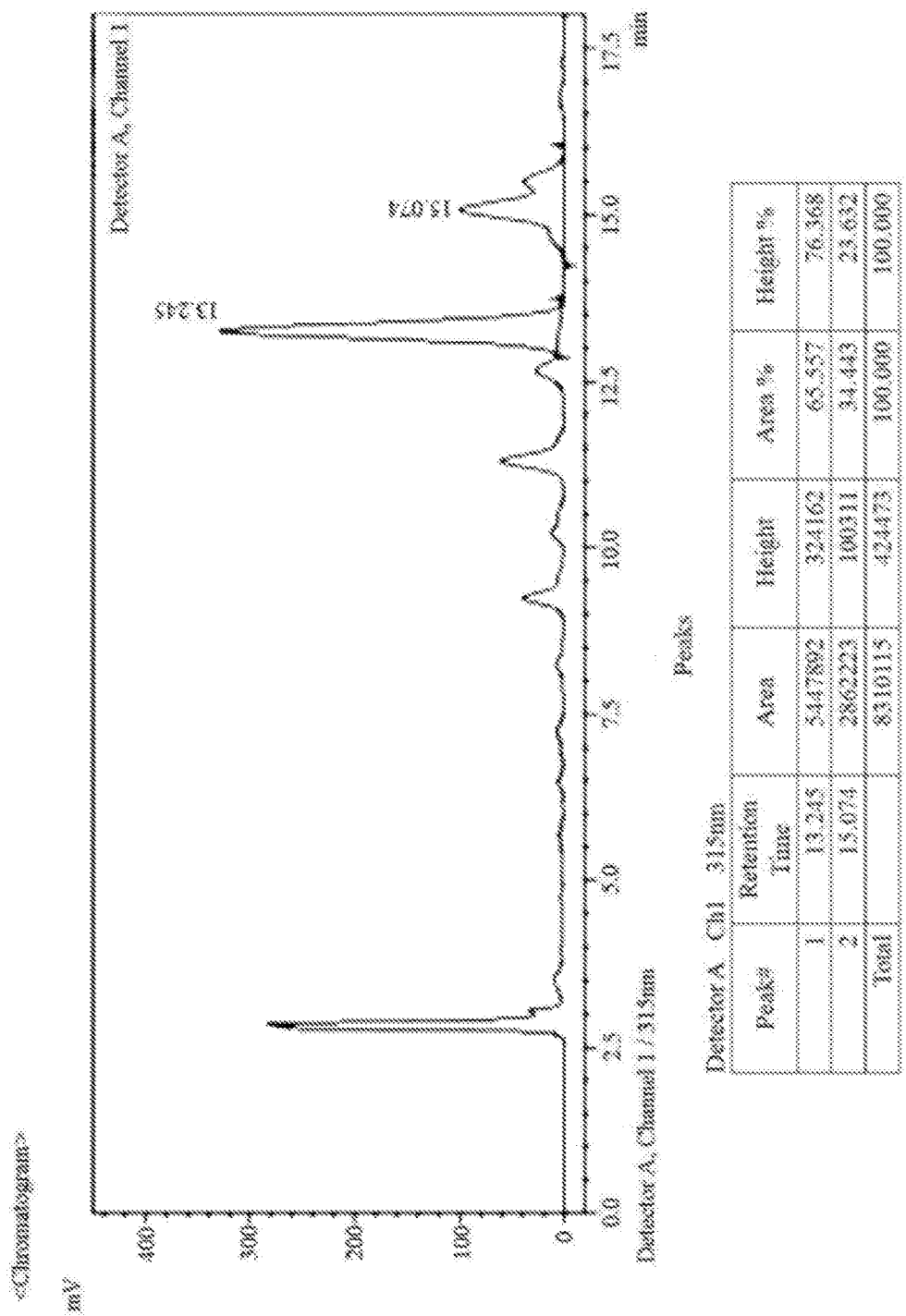

10.4 g of acetate ester of hexahydro-β-acid was dissolved in 80 ml of 95% ethanol. The resulting solution was cooled to 0° C., and added with 200 ml of aqueous solution of 1% potassium hydroxide dropwise within about 0.5 h, followed by the addition of 4.5 g of cobalt chloride hexahydrate. Then the resulting mixture was stirred for 1 hour and filtrated. The filter cake was washed with water, and dried to give 8.0 g of brown solids (cobalt salt of acetate ester of hexahydro-β-acid), the yield of which is about 73% (FIG. 11).

Embodiment 4.6

Preparation of Manganese Salt of Acetate Ester of Hexahydro-β-acid (IST_011_008)

10.5 g of acetate ester of hexahydro-β-acid was dissolved in 80 ml of 95% ethanol. The resulting solution was cooled to −5° C., and added with 200 ml of aqueous solution of 1% potassium hydroxide dropwise within about 20 minutes. 1.9 g of manganese chloride was dissolved in 30 ml of water, and the resulting solution was added dropwise into the potassium solution. Then the resulting mixture was stirred for 1 hour and filtrated. The filter cake was washed with water, and dried to give of dark brown solids (manganese salt of acetate ester of hexahydro-β-acid), the yield of which is about 72%.

Embodiment 4.7

Preparation of Ferrous Salt of Acetate Ester of Hexahydro-β-acid (IST_011_010)

Figure 12:
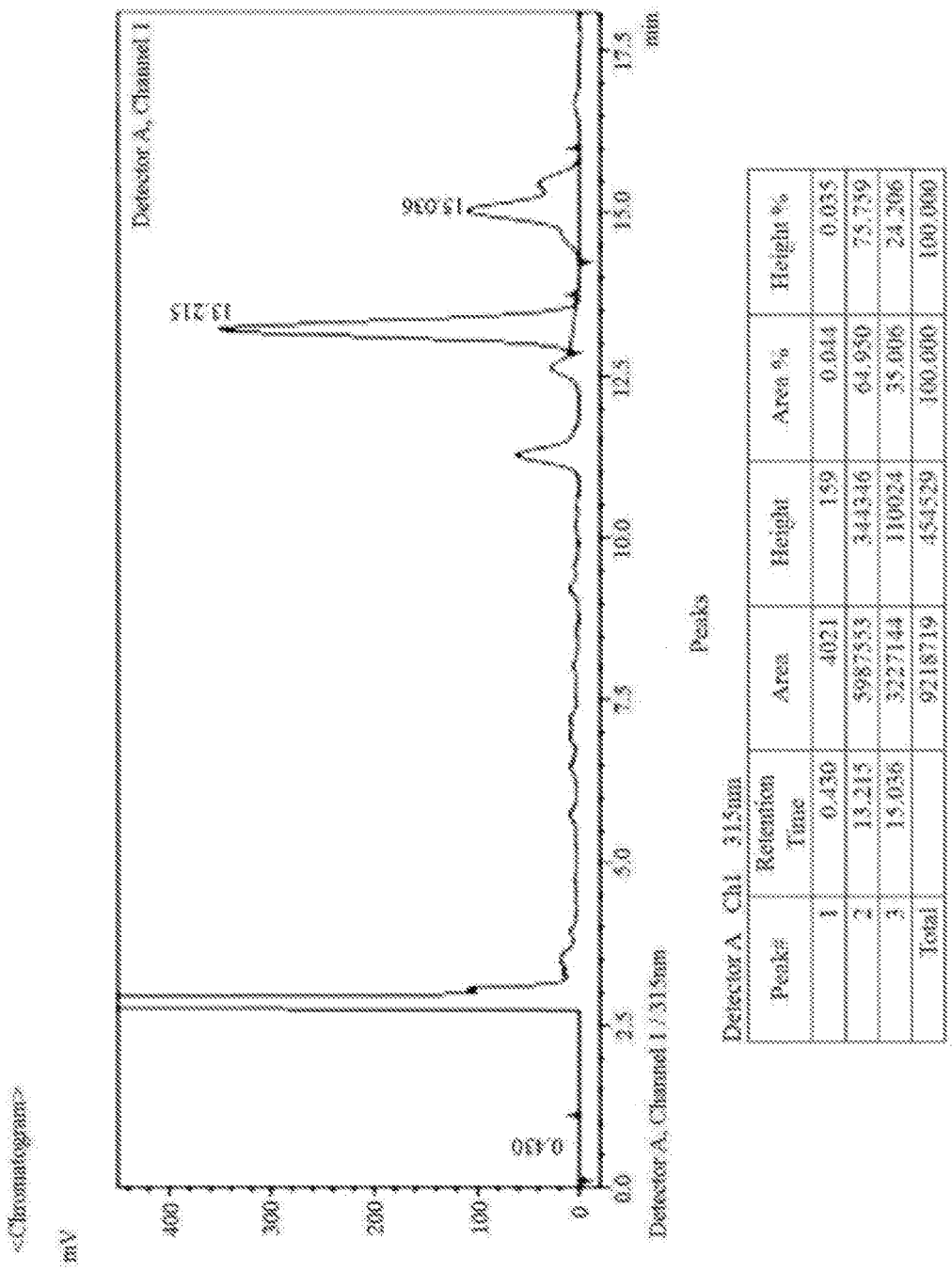

10.5 g of acetate ester of hexahydro-β-acid was dissolved in 80 ml of 95% ethanol. The resulting solution was cooled to −5° C., and added with 200 ml of aqueous solution of 1% potassium hydroxide dropwise within about 20 minutes. 5.0 g of $FeSO_4.7H_2O$ was dissolved in 30 ml of water, and the resulting solution was added dropwise into the potassium solution. Then the resulting mixture was stirred for 1 hour and filtrated. The filter cake was washed with water, and dried to give 5.0 g of red-brown solids (manganese salt of acetate ester of hexahydro-β-acid), the yield of which is about 45% (FIG. 12).

Embodiment 5

Synthesis of Monoesters of Hexahydro-β-acid (IST_011)

Various monoester derivatives of hexahydro-β-acid were formed by the reaction between hexahydro-β-acid and acyl chloride with triethylamine as alkali and dichloride methane as solvent. Following is a schematic of the preparation of the target ester derivatives. Water should be prevented from involving in the preparation.

Reaction equation:

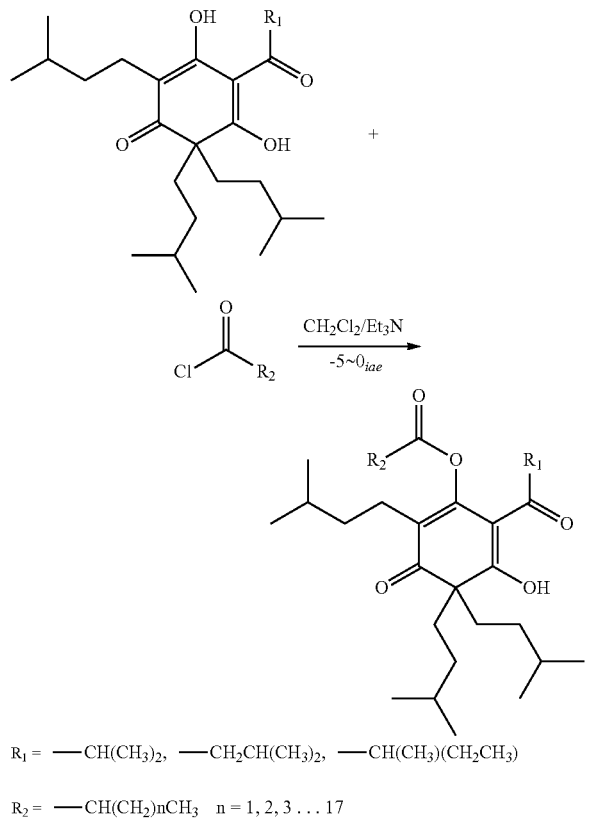

$R_1 =$ —$CH(CH_3)_2$, —$CH_2CH(CH_3)_2$, —$CH(CH_3)(CH_2CH_3)$ $R_2 =$ —$CH(CH_2)nCH_3$   $n = 1, 2, 3 \ldots 17$ Embodiment 5.1

Preparation of Mono Acetate Ester of Hexahydro-β-acid (IST_011_001)

Figure 13:
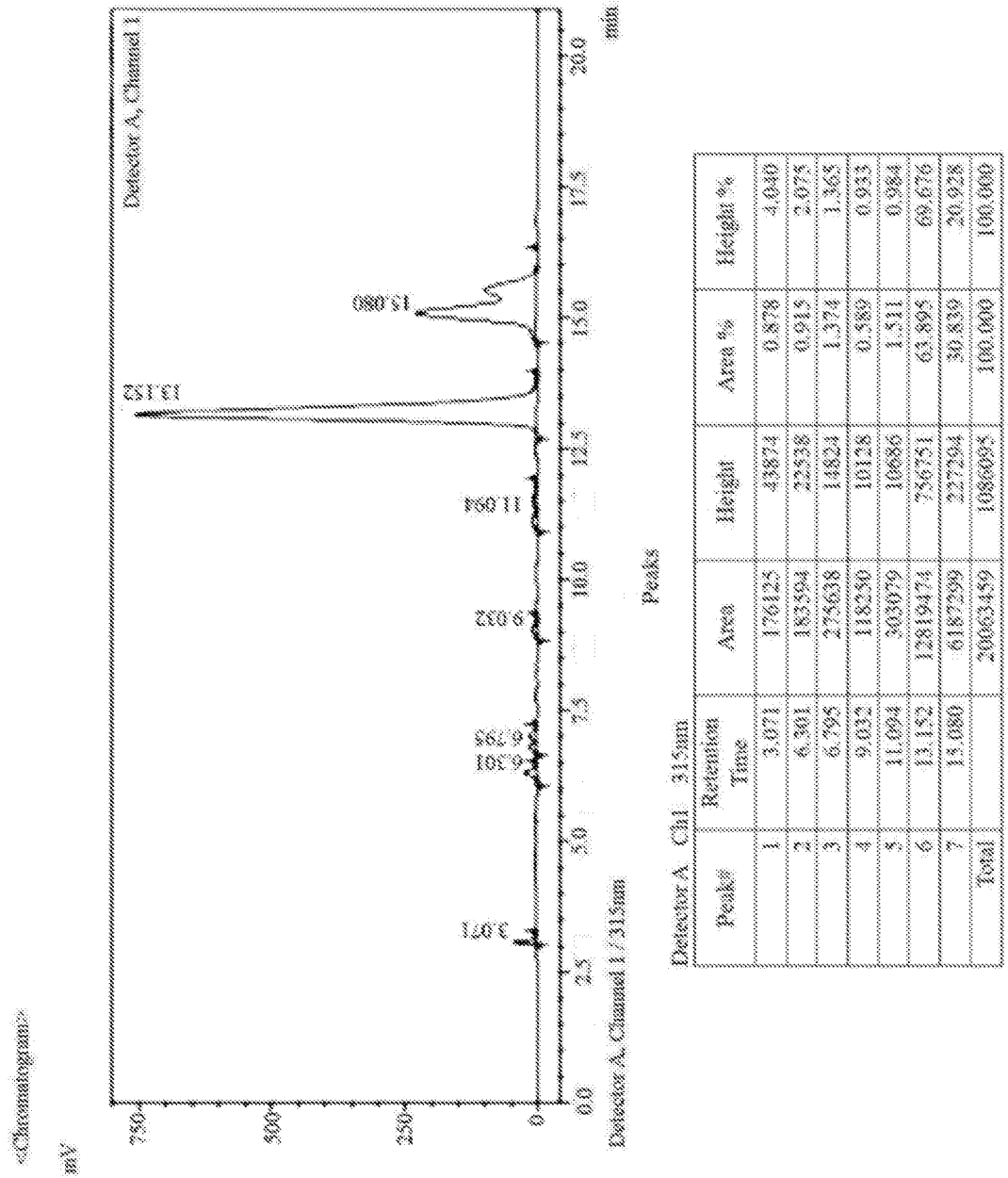

20 g of hexahydro-β-acid (with a molecular weight of 420) was dissolved in 200 ml of dichloride methane, followed by the addition of 4.8 g of triethylamine (with a molecular weight of 101.19). The resulting mixture was cooled to −5~0° C. with stilling. 3.9 g of acetyl chloride (with a molecular weight of 78.5) was dissolved in 20 ml of dichloride methane, and the resulting solution was added dropwise into the hexahydro-β-acid solution within 0.5 h. Then the reaction was continued for 1 hour, monitored by HPLC. The mixture was then let stand until room temperature, added with 40 ml of pure water, stirred, and the layers were separated. The organic phase was washed with 100 ml of water for three times, dried over anhydrous sodium sulfate, and subjected to decompression to remove the solvent and give 22.6 g of oily product (mono acetate ester of hexahydro-β-acid), the yield of which is 104% (FIG. 13).

Embodiment 5.2

Preparation of Mono Decanoate Ester of Hexahydro-β-acid (IST_011_002)

Figure 14:
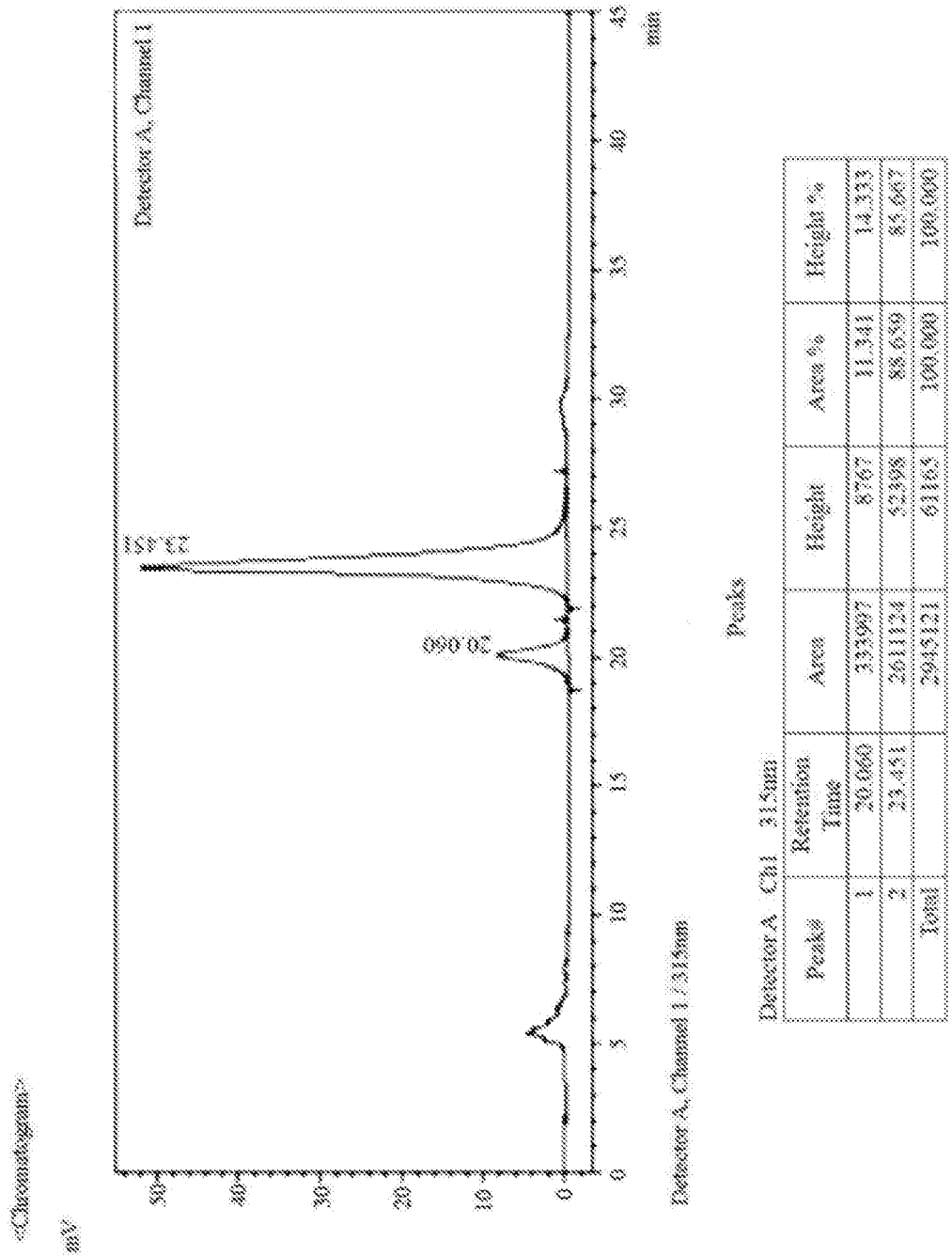

20.4 g of hexahydro-β-acid (with a molecular weight of 420) was dissolved in 100 ml of dichloride methane, followed by the addition of 4.8 g of triethylamine with a molecular weight of 101.19). The resulting mixture was cooled to −5~0° C. with stirring. 9.8 g of decanoly chloride (molecular weight: 190.71, d: 0.92) was dissolved in 50 ml of dichloride methane, and the resulting solution was added dropwise into the hexahydro-β-acid solution within 0.5 h. Then the reaction was continued for 1 hour, monitored by TLC. The mixture was then let stand until room temperature, added with 40 ml of pure water, stirred, and the layers were separated. The organic phase was washed with 50 ml of water for three times, dried over anhydrous sodium sulfate, decolored on silica gel, and the solvent was removed to give 27.5 g of oily product (mono decanoate ester of hexahydro-β-acid), the yield of which is 102% (FIG. 14).

Embodiment 5.3

Preparation of Mono Stearate Ester of Hexahydro-β-acid (IST_011_003)

Figure 15:
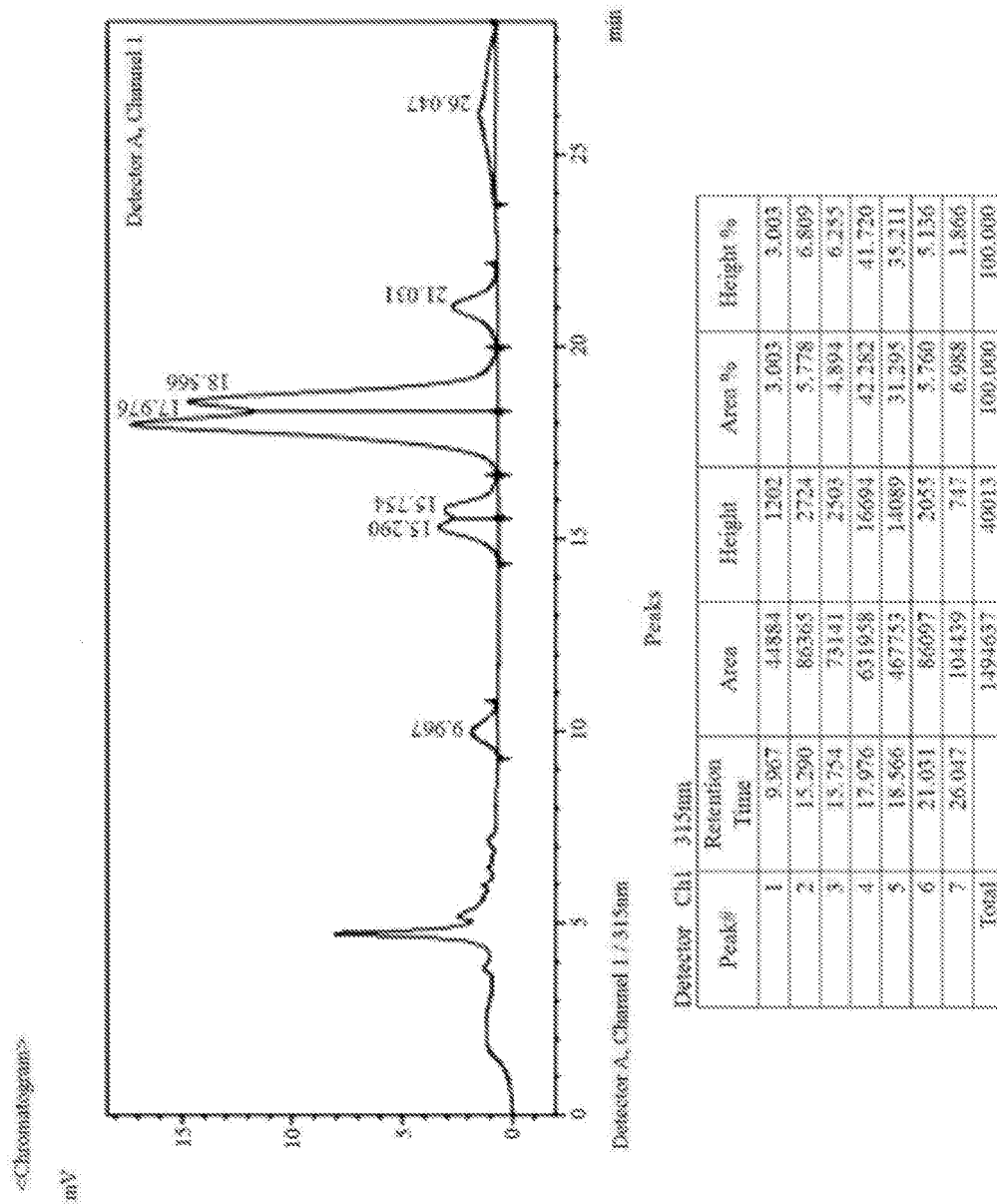

10.0 g of hexahydro-β-acid (with a molecular weight of ~420) was dissolved in 40 ml of dichloride methane, followed by the addition of stearoyl chloride (with a molecular weight of 302.9). The resulting mixture was cooled to 0° C. 2.4 g of triethylamine (with a molecular weight of 101.19) was dissolved in 6 ml of dichloride methane, and the resulting solution was added dropwise into the hexahydro-β-acid solution within 0.5 h. The reaction was continued for 2 hours, monitored by TLC. The mixture was then let stand until room temperature, and added with 50 ml of pure water. No distinct liquid-separation was observed. Then the mixture was added with 5 g of sodium chloride and stirred, the layers were separated. The organic phase was dried over anhydrous sodium sulfate, and then the solvent was removed, to give 16.9 g of oily product (mono stearate ester of hexahydro-β-acid), the yield of which is 103% (FIG. 15).

Embodiment 5.4

Preparation of Butyrate Ester Hexahydro-β-acid (IST_011_018)

Figure 16:
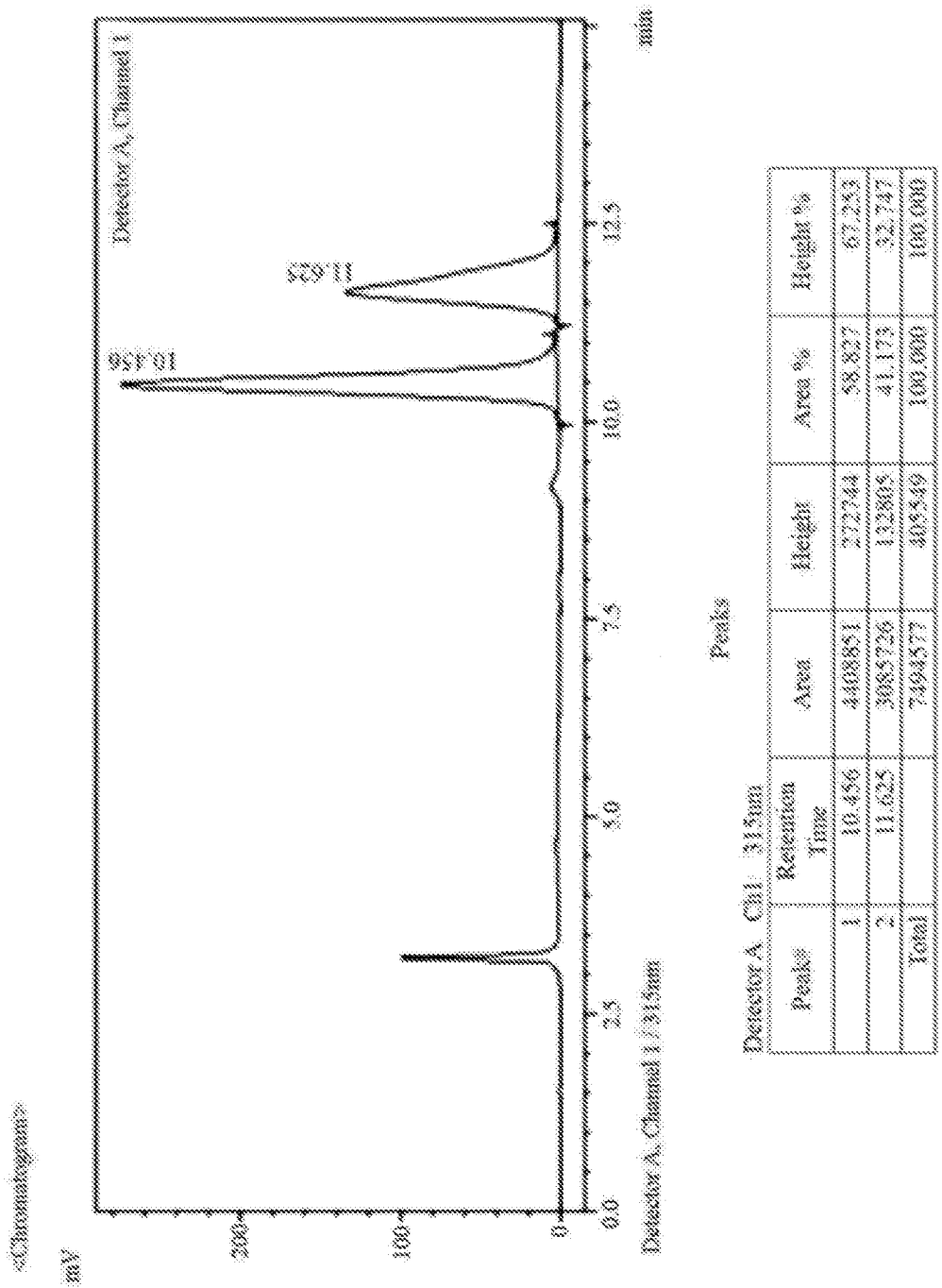

5.0 g of hexahydro-β-acid (with a molecular weight of ~420) was dissolved in 40 ml of dichloride methane, followed by the addition of 1.8 g of butyryl chloride (with a molecular weight of 106.6). The resulting mixture was cooled to 0° C. 3 ml of triethylamine with a molecular weight of 101.19) was dissolved in 6 ml of dichloride methane, and the resulting solution was added dropwise into the hexahydro-β-acid solution within 0.5 h. Then the reaction was continued for 2 hours, monitored by TLC. The mixture was then let stand until room temperature, added with 50 ml of pure water, stirred, and the layers were separated. The organic phase was dried over anhydrous sodium sulfate, and the solvent was removed. Then a column chromatography was performed to give 2.4 g of oily product (butyrate ester of hexahydro-β-acid), the yield of which is 40% (FIG. 16).

Embodiment 5.5

Preparation of Caprylate Ester of Hexahydro-β-acid (IST_011_019)

Figure 17:
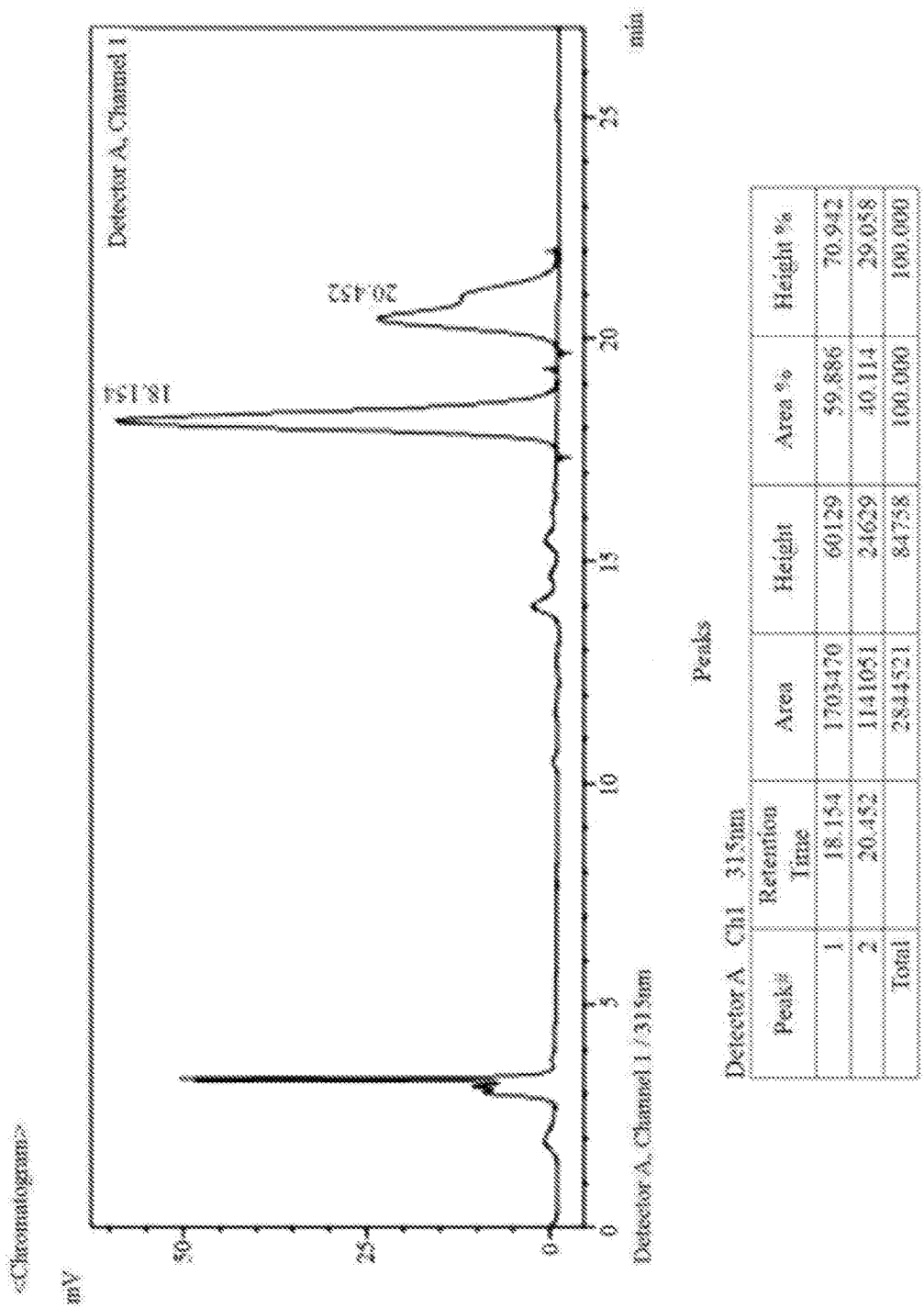

5.0 g of hexahydro-β-acid (with a molecular weight of ~420) was dissolved in 40 ml of dichloride methane, followed by the addition of 2.9 g of caprylyl chloride (with a molecular weight of 162.6). The resulting mixture was cooled to 0° C. 3 ml of triethylamine (with a molecular weight of 101.19) was dissolved in 6 ml of dichloride methane, and the resulting solution was added dropwise into the hexahydro-β-acid solution within 0.5 h. Then the reaction was continued for 2 hours, monitored by TLC. The mixture was then let stand until room temperature, added with 50 ml of pure water, stirred, and the layers were separated. The organic phase was dried over anhydrous sodium sulfate, and the solvent was removed. Then a column chromatography was performed to give 3 g of oily product (caprylate ester of hexahydro-β-acid), the yield of which is 46% (FIG. 17).

Embodiment 5.6

Preparation of Laurate Ester of Hexahydro-β-acid (IST_011_020)

Figure 18:
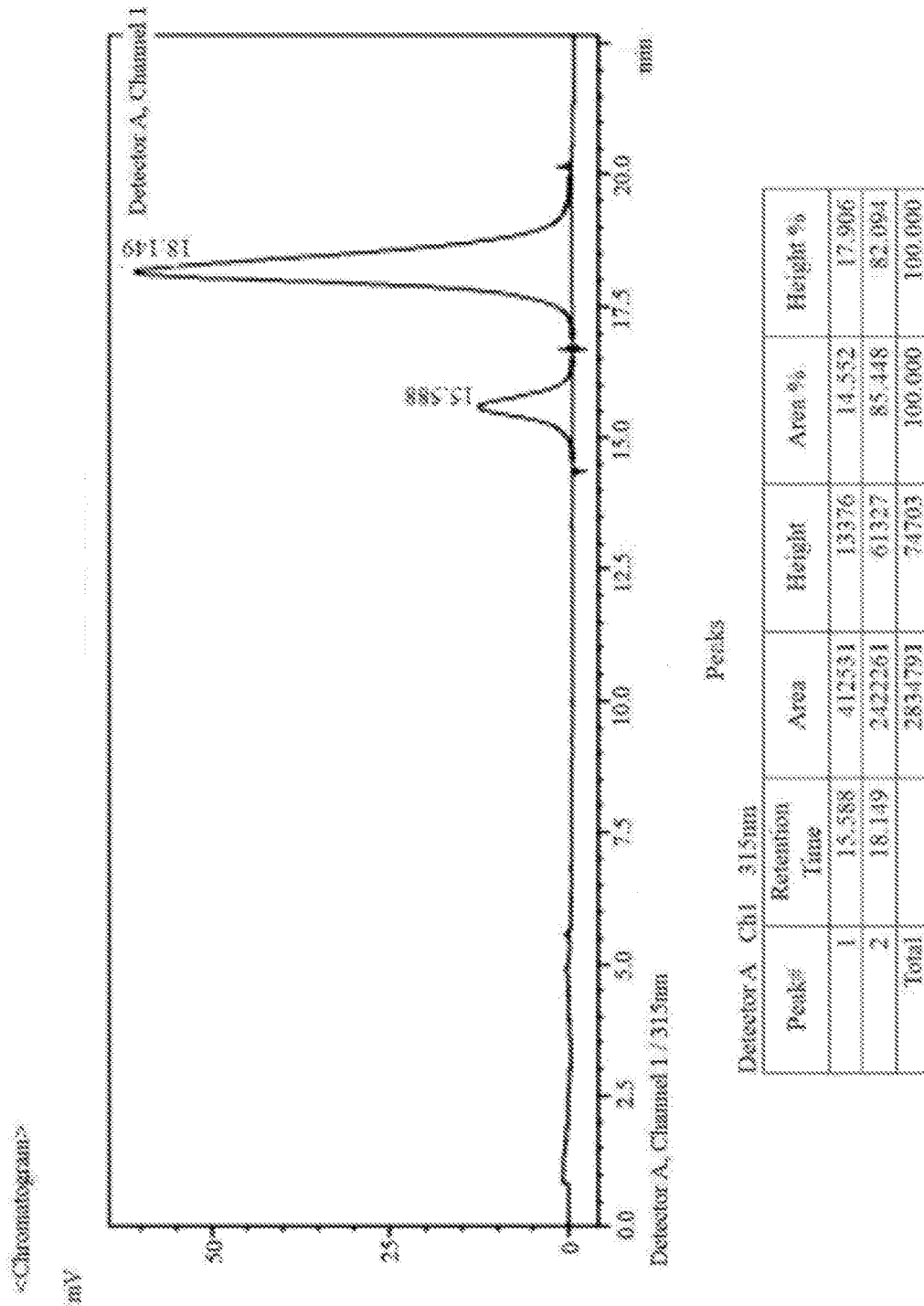

5.0 g of hexahydro-β-acid (with a molecular weight of ~420) was dissolved in 40 ml of dichloride methane, followed by the addition of 4.2 ml of lauroyl chloride (with a molecular weight of 218.8). The resulting mixture was cooled to 0° C. 3 ml of triethylamine (with a molecular weight of 101.19) was dissolved in 6 ml of dichloride methane, and the resulting solution was added dropwise into the hexahydro-β-acid solution within 0.5 h. Then the reaction was continued for 2 hours, monitored by TLC. The mixture was then let stand until room temperature, added with 50 ml of pure water, stirred, and the layers were separated. The organic phase was dried over anhydrous sodium sulfate, and the solvent was removed. Then a column chromatography was performed to give 4 g of oily product (laurate ester of hexahydro-β-acid), the yield of which is 53% (FIG. 18).

Embodiment 5.7

Preparation of Cetylate Ester of Hexahydro-β-acid (IST_011_021)

Figure 19:
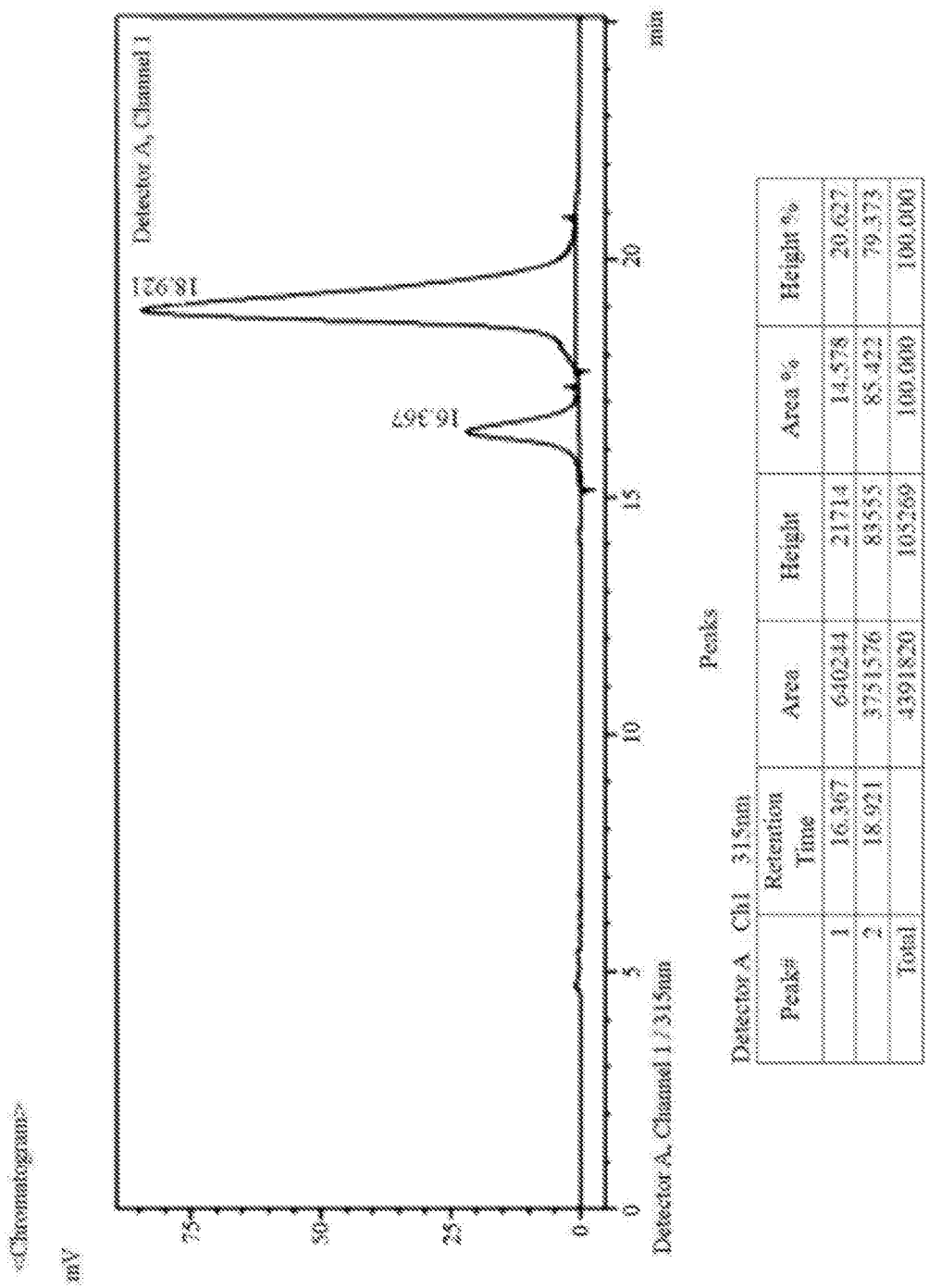

5.0 g of hexahydro-β-acid (with a molecular weight of ~420) was dissolved in 40 ml of dichloride methane, followed by the addition of 5.5ml of palmitic chloride (with a molecular weight of 274.9). The resulting mixture was cooled to 0° C. 3 ml of triethylamine (with a molecular weight of 101.19) was dissolved in 6 ml of dichloride methane, and the resulting solution was added dropwise into the hexahydro-β-acid solution within 0.5 h. Then the reaction was continued for 2 hours, monitored by TLC. The mixture was then let stand until room temperature, added with 50 ml of pure water, stirred, and the layers were separated. The organic phase was dried over anhydrous sodium sulfate, and the solvent was removed. Then a column chromatography was performed to give 3.5 g of oily product (cetylate ester of hexahydro-β-acid), the yield of which is 44% (FIG. 19).

Embodiment 6

Thermo Stability Test of Esters and/or Salts of Hexahydro-β-acid

The esters and/or salts of hexahydro-β-acid prepared in the above embodiments were mixed with corncob powder to obtain premixes with a mass fraction of 2%. Samples (the premixes) were placed in crucibles, and then placed in oven at 100° C. for different durations. Then 1.0 g of each of the samples (three duplicate samples from each sample) and 50 ml of ethanol were added into a conical flask, followed by the addition of 100 μL of concentrated hydrochloric acid. The mixture was then subjected to sonication for 5 minutes, and then filtrated. The filtrate was transferred into a 50 ml volumetric flask, topped up to the final volume with ethanol, and then filtered with a 0.45 μm microporous membrane and subjected to HPLC analysis.

Results of the stability test were as shown in table 1. Results showed that the thermal stability of each of the esters and/or salts of hexahydro-β-acid was enhanced.

TABLE 1

Change of the main component of the esters and/or salts of hexahydro-β-acid after being heated at 100° C. for different durations

| Compound | Initial content (%) | Content when being heated at 100° C. for 20 h (%) | Content when being heated at 100° C. for 44 h (%) |
| --- | --- | --- | --- |
| Hexahydro-β-acid | 2.0 | 0.06 | 0 |
| Mono acetate ester of hexahydro-β-acid | 2.0 | 1.52 | 1.11 |
| Mono decanoate ester of hexahydro-β-acid | 2.0 | 1.93 | 1.82 |
| Copper salt of acetate ester of hexahydro-β-acid | 2.0 | 1.50 | 1.28 |
| Magnesium salt of acetate ester of hexahydro-β-acid | 2.0 | 1.42 | 0.7 |
| Calcium salt of acetate ester of hexahydro-β-acid | 2.0 | 1.21 | 0.31 |
| Zinc salt of acetate ester of hexahydro-β-acid | 2.0 | 1.64 | 0.70 |
| Manganese salt of acetate ester of hexahydro-β-acid | 2.0 | 0 | 0 |
| Cobalt salt of acetate ester of hexahydro-β-acid | 2.0 | 0.17 | 0.12 |
| Ferrous salt of acetate ester of hexahydro-β-acid | 7.0 | 1.69 | 1.63 |
| Magnesium salt of hexahydro-β-acid | 2.0 | 1.49 | 0.91 |
| Calcium salt of hexahydro-β-acid | 7.0 | 0.35 | 0.09 |
| Zinc salt of hexahydro-β-acid | 2.0 | 0.95 | 0.52 |
| Ferrous salt of hexahydro-β-acid | 2.0 | 0.14 | 0.05 |
| Butyrate ester of hexahydro-β-acid | 2.0 | 1.74 | 0.69 |
| Caprylate ester of hexahydro-β-acid | 2.0 | 2.0 | 1.51 |
| Laurate ester of hexahydro-β-acid | 2.0 | 2.0 | 1.96 |
| Cetylate ester of hexahydro-β-acid | 2.0 | 1.98 | 1.93 |

Embodiment 7

Application Effect in Broiler Feed 500 1-day-aged, healthy, fast-grown yellow feather broilers (female) in the same growing state and similar in weight were randomly divided into five groups according to table 2, 100 broilers in each group. Broilers of each group were fed with different dosages of mono decanoate ester of hexahydro-β-acid or hexahydro-β-acid.

The broilers were kept in cages and fed with food and water ad libitum during a 30 days test period, wherein weight gain and feed conversion efficiency of the broilers fed with mono decanoate ester of hexahydro-β-acid had been significantly improved, and improvement of the productivity of the broilers fed with mono decanoate ester of hexahydro-β-acid was more significant than that of the broilers fed with hexahydro-β-acid in the same dosage (table 3).

TABLE 2

Grouping of tested animals, and dosage of additives

| Group | Quantity of the broilers | Additive | Dosage | Administration |
|---|---|---|---|---|
| 1 | 100 | — | — | — |
| 2 | 100 | Hexahydro-β-acid | 2 ppm | Mixed with feed |
| 3 | 100 | Mono decanoate ester of hexahydro-β-acid | 2 ppm | Mixed with feed |
| 4 | 100 | Hexahydro-β-acid | 20 ppm | Mixed with feed |
| 5 | 100 | Mono decanoate ester of hexahydro-β-acid | 20 ppm | Mixed with feed |

—: control blank, wherein neither mono decanoate ester of hexahydro-β-acid nor hexahydro-β-acid was added

TABLE 3

Application effect of mono decanoate ester of hexahydro-β-acid and hexahydro-β-acid in broiler feed

| Group | Initial weight (g) | Survival rate (%) | Average weight gain (g) | Consumption (kg) | Average daily weight gain (g) | Feed conversion efficiency |
|---|---|---|---|---|---|---|
| 1 | 39.0 | 100 | 738 | 154.64 | 24.6 | 2.09 |
| 2 | 39.0 | 100 | 745 | 147.76 | 24.83 | 1.983 |
| 3 | 39.3 | 100 | 768 | 147.94 | 25.6 | 1.926 |
| 4 | 39.2 | 100 | 758 | 149.18 | 25.26 | 1.968 |
| 5 | 39.5 | 100 | 797 | 146.42 | 26.57 | 1.837 |

Embodiment 8

Application Effect in Pig Feed 120 67-day-aged, Duroc-Yorkshire-Landrace crossbred lean pigs similar in weight were randomly divided into six groups, 20 pigs in each group. Pigs in each group were fed with mono cetylate ester of hexahydro-β-acid with the types and the dosages listed in table 4. The pigs were fed with food and water ad libitum for 14 days, wherein weight gain and feed conversion efficiency of the pigs fed with mono cetylate ester of hexahydro-β-acid had been significantly improved. Grouping and results of the trial were as shown in table 4 and table 5.

TABLE 4

Grouping of the animals, and dosages of additives

| Group | Quantity of the pigs | Additive | Dosage (mg/kg) | Administration |
|---|---|---|---|---|
| 1 | 20 | — | — | — |
| 2 | 20 | — | — | — |
| 3 | 20 | Cetylate ester of hexahydro-β-acid | 5 | Mixed with feed |
| 4 | 20 | Cetylate ester of hexahydro-β-acid | 25 | Mixed with feed |
| 5 | 20 | Cetylate ester of hexahydro-β-acid | 5 | Mixed with feed |
| 6 | 20 | Cetylate ester of hexahydro-β-acid | 25 | Mixed with feed |

TABLE 5

Application effect of cetylate ester of hexahydro-β-acid in pig feed

| Group | Average initial weight (kg) | Average weight gain (kg) | Average daily weight gain (kg/day) | Consumption (kg) | Feed conversion efficiency |
|---|---|---|---|---|---|
| 1 | 17.01 | 5.875 | 0.419 | 271.3 | 2.309 |
| 2 | 16.87 | 5.685 | 0.406 | 257.9 | 2.269 |
| 3 | 17.53 | 7.18 | 0.512 | 298.4 | 2.078 |
| 4 | 17.74 | 7.985 | 0.570 | 272.5 | 1.706 |
| 5 | 17.02 | 7.11 | 0.508 | 277.2 | 1.949 |
| 6 | 17.81 | 8.12 | 0.580 | 274.5 | 1.690 |

The invention claimed is:

1. Inner complex salts of hexahydro-β-acid, having a structural formula as shown in formula (I):

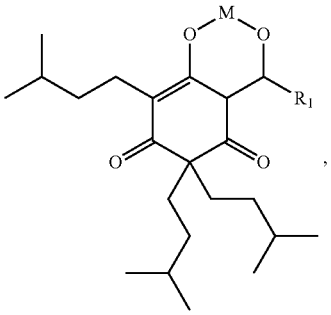

formula (I)

wherein $R_1$ is isopropyl, isobutyl or sec-butyl; and
wherein M is a divalent metal ion of copper, zinc, manganese, cobalt, iron, calcium or magnesium.

2. Acetate ester salts of hexahydro-β-acid, having a structural formula as shown in formula (II):

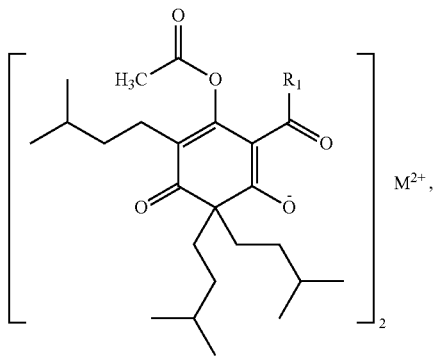

formula (II)

wherein $R_1$ is isopropyl, isobutyl or sec-butyl; and
wherein M is a divalent metal ion of copper, zinc, manganese, cobalt, iron, calcium or magnesium.

3. Monoesters of hexahydro-β-acid, having a structural formula as shown in formula (III):

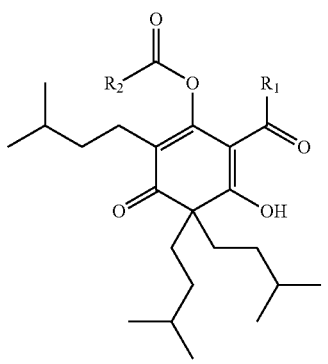

formula (III)

wherein $R_1$ is isopropyl, isobutyl or sec-butyl;
wherein $R_2$ is —$(CH_2)_nCH_3$, and
wherein n=0 to 16.

4. An animal growth-promoting feed additive composition, comprising:
the inner complex salts of hexahydro-β-acid according to claim 1.

5. An animal growth-promoting feed additive composition, comprising:
the acetate ester salts of hexahydro-β-acid according to claim 2.

6. An animal growth-promoting feed additive composition, comprising:
the monoesters of hexahydro-β-acid according to claim 3.

7. A method of feeding an animal, comprising:
administering a feed comprising an animal growth-promoting feed additive comprising the inner complex salts of hexahydro-β-acid according to claim 1 to an animal.

8. The method of claim 7, wherein the animal is a pig, chicken, duck, goose, beef cattle, dairy cattle, sheep, fish, shrimp, fox, marten or raccoon dog.

9. The method of claim 7, wherein the inner complex salts of hexahydro-β-acid are provided at an additive dosage of 0.1 to 200 ppm.

10. A method of feeding an animal, comprising:
administering a feed comprising an animal growth-promoting feed additive comprising the acetate ester salts of hexahydro-β-acid according to claim 2 to an animal.

11. The method of claim 10, wherein the animal is a pig, chicken, duck, goose, beef cattle, dairy cattle, sheep, fish, shrimp, fox, marten or raccoon dog.

12. The method of claim 10, wherein the acetate ester salts of hexahydro-β-acid are provided at an additive dosage of 0.1 to 200 ppm.

13. A method of feeding an animal, comprising:
administering a feed comprising an animal growth-promoting feed additive comprising the monoesters of hexahydro-β-acid according to claim 3 to an animal.

14. The method of claim 12, wherein the animal is a pig, chicken, duck, goose, beef cattle, dairy cattle, sheep, fish, shrimp, fox, marten or raccoon dog.

15. The method of claim 12, wherein the monoesters of hexahydro-β-acid are provided at an additive dosage of 0.1 to 200 ppm.

* * * * *